United States Patent
Schmidt et al.

(10) Patent No.: US 7,420,677 B2
(45) Date of Patent: Sep. 2, 2008

(54) SENSING PHOTON ENERGIES OF OPTICAL SIGNALS

(75) Inventors: Oliver Schmidt, Palo Alto, CA (US); Peter Kiesel, Palo Alto, CA (US); Noble M. Johnson, Menlo Park, CA (US); Patrick Y. Maeda, Mountain View, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 309 days.

(21) Appl. No.: 11/315,926

(22) Filed: Dec. 22, 2005

(65) Prior Publication Data

US 2007/0147189 A1    Jun. 28, 2007

(51) Int. Cl.
*G01J 3/51*    (2006.01)

(52) U.S. Cl. .................. 356/417; 356/419; 250/226

(58) Field of Classification Search ............ 356/317, 356/417, 416, 419
See application file for complete search history.

(56) References Cited

U.S. PATENT DOCUMENTS

| | | |
|---|---|---|
| 2,708,389 A | 5/1955 | Kavanagh |
| 3,973,118 A | 8/1976 | LaMontagne |
| 4,081,277 A | 3/1978 | Brault et al. |
| 4,514,257 A | 4/1985 | Karlsson et al. |
| 4,573,796 A | 3/1986 | Martin et al. |
| 4,764,670 A | 8/1988 | Pace et al. |
| 4,957,371 A | 9/1990 | Pellicori et al. |
| 4,976,542 A | 12/1990 | Smith |
| 5,144,498 A | 9/1992 | Vincent |
| 5,166,755 A | 11/1992 | Gat |
| 5,305,082 A | 4/1994 | Bret |
| 5,324,401 A | 6/1994 | Yeung et al. |
| 5,370,842 A | 12/1994 | Miyazaki et al. |
| 5,572,328 A | 11/1996 | Fouckhardt et al. |
| 5,682,038 A | 10/1997 | Hoffman |
| 5,777,329 A | 7/1998 | Westphal et al. |
| 5,784,507 A | 7/1998 | Holm-Kennedy et al. |

(Continued)

FOREIGN PATENT DOCUMENTS

EP    1324018 A2    7/2003

(Continued)

OTHER PUBLICATIONS

Adams, M.L., Enzelberger, M., Quake, S., and Scherer, A., "Microfluidic integration on detector arrays for absorption and fluorescence micro-spectrometers," Sensors and Actuators A, vol. 104, 2003, pp. 25-31.

(Continued)

*Primary Examiner*—F. L Evans
(74) *Attorney, Agent, or Firm*—James T. Beran; Leading-Edge Law Group, PLC

(57) ABSTRACT

An integrated circuit includes a photosensor array with subrange cells that photosense within respective subranges of an energy range. An optical signal and the array move relative to each other, and, for segments of their relative movement, sets of subrange cells photosense within subranges that are different. For example, a scanning device can cause relative scanning movement. The optical signal can be produced by illuminating a two-dimensional object. The photosensed quantities for a part of the optical signal can be used to produce spectral information for the part.

33 Claims, 13 Drawing Sheets

U.S. PATENT DOCUMENTS

| | | |
|---|---|---|
| 5,792,663 A | 8/1998 | Fry et al. |
| 5,801,831 A | 9/1998 | Sargoytchev |
| 5,864,641 A | 1/1999 | Murphy et al. |
| 5,876,674 A | 3/1999 | Dosoretz et al. |
| 5,880,474 A | 3/1999 | Norton et al. |
| 5,945,676 A | 8/1999 | Khalil et al. |
| 6,040,578 A | 3/2000 | Malin et al. |
| 6,091,502 A | 7/2000 | Weigl et al. |
| 6,137,117 A | 10/2000 | Feldstein et al. |
| 6,192,168 B1 | 2/2001 | Feldstein et al. |
| 6,249,346 B1 | 6/2001 | Chen et al. |
| 6,275,628 B1 | 8/2001 | Jones et al. |
| 6,295,130 B1 | 9/2001 | Sun et al. |
| 6,353,475 B1 | 3/2002 | Jensen et al. |
| 6,399,405 B1 | 6/2002 | Chen et al. |
| 6,405,073 B1 | 6/2002 | Crowley et al. |
| 6,429,022 B1 | 8/2002 | Kunz et al. |
| 6,459,080 B1 | 10/2002 | Yin et al. |
| 6,483,959 B1 | 11/2002 | Singh et al. |
| 6,490,034 B1 | 12/2002 | Woias et al. |
| 6,505,775 B1 | 1/2003 | Gu et al. |
| 6,519,037 B2 | 2/2003 | Jung et al. |
| 6,525,308 B1 | 2/2003 | Schmidt-Hattenberger |
| 6,558,945 B1 | 5/2003 | Kao |
| 6,577,780 B2 | 6/2003 | Lockhart |
| 6,580,507 B2 | 6/2003 | Fry et al. |
| 6,603,548 B2 | 8/2003 | Church et al. |
| 6,608,679 B1 | 8/2003 | Chen et al. |
| 6,630,999 B2 | 10/2003 | Shroder |
| 6,700,664 B1 | 3/2004 | Honda et al. |
| 6,781,690 B2 | 8/2004 | Armstrong et al. |
| 6,785,002 B2 | 8/2004 | Zarrabian et al. |
| 6,800,849 B2 | 10/2004 | Staats |
| 6,867,420 B2 | 3/2005 | Mathies et al. |
| 6,870,149 B2 | 3/2005 | Berezin |
| 6,887,713 B2 | 5/2005 | Nelson et al. |
| 7,106,441 B2 | 9/2006 | Sun et al. |
| 7,149,396 B2 | 12/2006 | Schmidt et al. |
| 7,248,361 B2 | 7/2007 | Kiesel et al. |
| 7,268,868 B2 | 9/2007 | Kiesel et al. |
| 7,291,824 B2 | 11/2007 | Kiesel et al. |
| 7,310,153 B2 | 12/2007 | Kiesel et al. |
| 7,315,667 B2 | 1/2008 | Schmidt et al. |
| 7,358,476 B2 | 4/2008 | Kiesel et al. |
| 2002/0155485 A1 | 10/2002 | Kao |
| 2003/0000835 A1 | 1/2003 | Witt et al. |
| 2003/0020915 A1 | 1/2003 | Schueller et al. |
| 2003/0077660 A1 | 4/2003 | Pien et al. |
| 2003/0235924 A1 | 12/2003 | Adams et al. |
| 2004/0027462 A1 | 2/2004 | Hing |
| 2004/0031684 A1 | 2/2004 | Witt |
| 2004/0032584 A1 | 2/2004 | Honda et al. |
| 2004/0038386 A1 | 2/2004 | Zesch et al. |
| 2004/0067167 A1 | 4/2004 | Zhang et al. |
| 2004/0132214 A1 | 7/2004 | Lin et al. |
| 2004/0141884 A1 | 7/2004 | Unno et al. |
| 2004/0145738 A1 | 7/2004 | Sun et al. |
| 2004/0175734 A1 | 9/2004 | Stahler et al. |
| 2004/0223881 A1 | 11/2004 | Cunningham et al. |
| 2004/0248318 A1 | 12/2004 | Weinberger et al. |
| 2005/0042615 A1 | 2/2005 | Smith et al. |
| 2005/0068526 A1 | 3/2005 | Avrutsky |
| 2005/0084203 A1 | 4/2005 | Kane |
| 2005/0099624 A1 | 5/2005 | Staehr et al. |
| 2005/0128479 A1 | 6/2005 | Gilbert et al. |
| 2006/0039009 A1 | 2/2006 | Kiesel et al. |
| 2006/0046312 A1 | 3/2006 | Kiesel et al. |
| 2006/0092413 A1 | 5/2006 | Kiesel et al. |
| 2006/0121555 A1 | 6/2006 | Lean et al. |
| 2006/0138313 A1 | 6/2006 | Tennant et al. |
| 2006/0274313 A1 | 12/2006 | Gilbert et al. |
| 2007/0070347 A1 | 3/2007 | Scherer et al. |
| 2007/0076210 A1 | 4/2007 | Kiesel et al. |
| 2007/0116609 A1 | 5/2007 | Baeuerle et al. |
| 2007/0145236 A1 | 6/2007 | Kiesel et al. |
| 2007/0145249 A1 | 6/2007 | Kielsel et al. |
| 2007/0146704 A1 | 6/2007 | Schmidt et al. |
| 2007/0146888 A1 | 6/2007 | Schmidt et al. |
| 2007/0147726 A1 | 6/2007 | Kiesel et al. |
| 2007/0147728 A1 | 6/2007 | Schmidt et al. |
| 2007/0148760 A1 | 6/2007 | Kiesel et al. |
| 2007/0201025 A1 | 8/2007 | Greenwald |

FOREIGN PATENT DOCUMENTS

| | | |
|---|---|---|
| EP | 1800752 A1 | 6/2007 |
| WO | WO 95/20144 | 7/1995 |
| WO | WO 99/44042 A2 | 9/1999 |
| WO | WO 00/62050 | 10/2000 |
| WO | WO 02/25269 A2 | 3/2002 |

OTHER PUBLICATIONS

Bernini, R., Campopiano, S., and Zeni, L., "Silicon Micromachined Hollow Optical Waveguides for Sensing Applications," IEE Jour. on Selected Topics in Quantum Electronics, vol. 8, No. 1, Jan./Feb. 2002, pp. 106-110.

Singh, K., Liu, C., Capjack, C., Rosmus, W., and Backhouse, C.J., "Analysis of cellular structure by light scattering measurements in a new cytometer design based on a liquid-core waveguide," IEEE Proc.-Nanobiotechnol., vol. 151, No. 1, Feb. 2004, pp. 10-16.

Office communication in U.S. Appl. No. 10/922,870, mailed Jul. 26, 2007, 11 pages, published in PAIR.

Office communication in U.S. Appl. No. 10/922,870, mailed Sep. 24, 2007, 3 pages, published in PAIR.

Amendment in U.S. Appl. No. 10/922,870, dated Apr. 30, 2007, 15 pages, published in PAIR.

Amendment in U.S. Appl. No. 10/922,870, dated Sep. 14, 2007, 9 pages, published in PAIR.

Amendment in U.S. Appl. No. 10/922,870, dated Oct. 4, 2007, 9 pages, published in PAIR.

Notice of Allowance and Fee(s) Due and attached papers for U.S. Appl. No. 10/922,870, mailed Oct. 22, 2007, 7 pages, published in PAIR.

Notice of Allowance and Fee(s) Due and attached papers for U.S. Appl. No. 11/315,387, mailed Jun. 20, 2007,23 pages, published in PAIR.

Notice of Allowance and Fee(s) Due and attached papers for U.S. Appl. No. 11/315,387, mailed Oct. 5, 2007, 7 pages, published in PAIR.

Amendment with Request for Continued Examination in U.S. Appl. No. 11/315,387, dated Sep. 18, 2007, 6 pages, published in PAIR.

Office communication in U.S. Appl. No. 11/316,660, mailed Mar. 8, 2007, 25 pages.

Amendment with Information Disclosure in U.S. Appl. No. 11/316,660, dated Jun. 6, 2007, 20 pages, published in PAIR.

Office communication in U.S. Appl. No. 11/316,660, mailed Oct. 19, 2007, 22 pages, published in PAIR.

Notice of Allowance and Fee(s) due and attached papers for U.S. Appl. No. 11/315,992, mailed Oct. 3, 2007, 19 pages, published in PAIR.

Communication from European Patent Office including extended European Search Report with European Search Report and Annex and European Search Opinion for counterpart EPO Application No. EPO 6126519, dated May 3, 2007, 7 pages.

Amendment with Information Disclosure in U.S. Appl. No. 11/316,660, dated Jan. 17, 2008, 15 pages, published in PAIR.

Rule 312 Amendment with Information Disclosure in U.S. Appl. No. 11/315,992, dated Dec. 27, 2007, 13 pages, published in PAIR.

Notice of Allowance and Fee(s) Due in U.S. Appl. No. 11/316,660, mailed Apr. 17, 2008, 16 pages, published in PAIR.

Office communication in U.S. Appl. No. 11/702,470, mailed Apr. 25, 2008, 22 pages.

FIG. 6
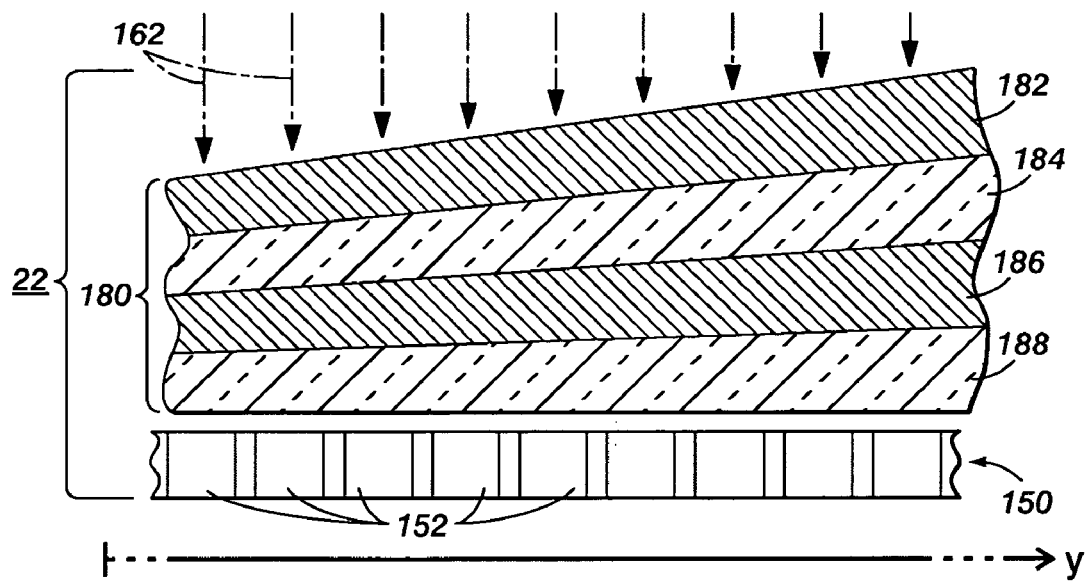
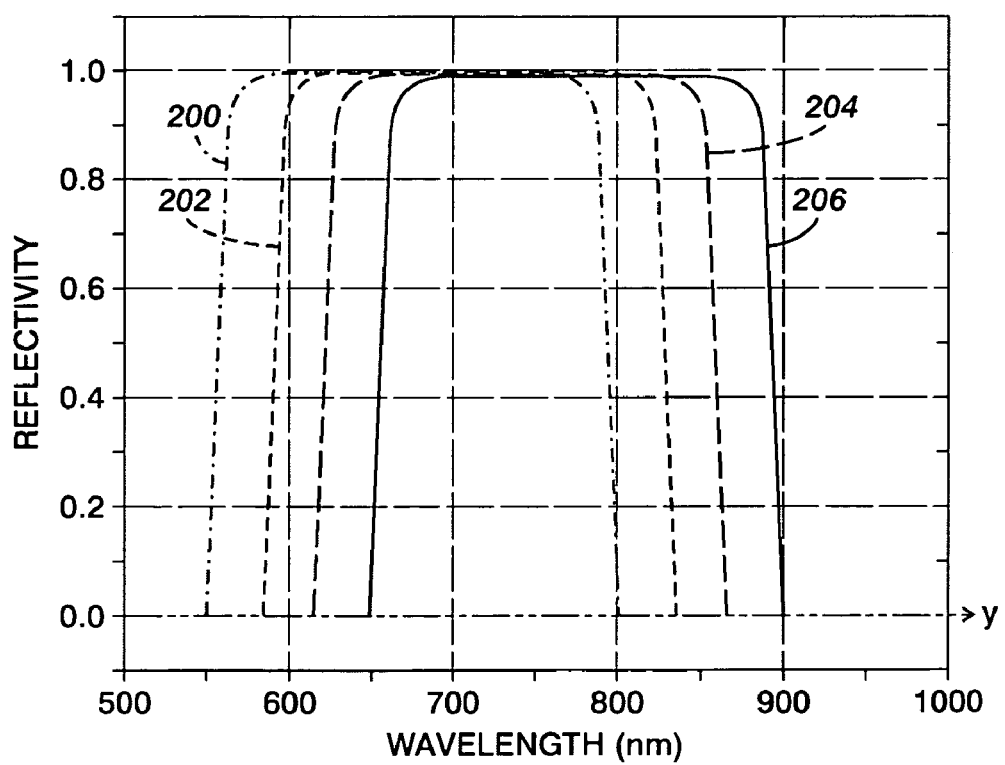
FIG. 7

SENSING PHOTON ENERGIES OF OPTICAL SIGNALS

The present application is related to the following copending applications, each of which is hereby incorporated by reference in its entirety: "Chip-Size Wavelength Detector", U.S. patent application Ser. No. 10/922,870, filed Aug. 23, 2004; "Anti-resonant Waveguide Sensors", U.S. patent application Ser. No. 10/976,434, filed Oct. 29, 2004; "Photosensing Throughout Energy Range and in Subranges", U.S. patent application Ser. No. 11/316,438, filed Dec. 22, 2005; "Sensing Photons From Objects in Channels", U.S. patent application Ser. No. 11/315,992, filed Dec. 22, 2005; "Providing Light To Channels Or Portions", U.S. patent application Ser. No. 11/316,660, filed Dec. 22, 2005; "Sensing Photon Energies Emanating from Channels or Moving Objects", U.S. patent application Ser. No. 11/315,386, filed Dec. 22, 2005; "Transmitting Light With Photon Energy Information", U.S. patent application Ser. No. 11/316,241, filed Dec. 22, 2005; "Obtaining Analyte Information", U.S. patent application Ser. No. 11/316,303, filed Dec. 22, 2005; and "Propagating Light to be Sensed", U.S. patent application Ser. No. 11/315,387, filed Dec. 22, 2005.

BACKGROUND OF THE INVENTION

The present invention relates generally to photosensing optical signals, and more particularly to photosensing photon energies of optical signals with photosensor arrays on integrated circuits (ICs).

U.S. Pat. No. 5,166,755 describes a spectrometer apparatus in which a spectrum resolving sensor contains an opto-electronic monolithic array of photosensitive elements and a continuous variable optical filter. The filter can include a variable thickness coating formed into a wedge shape on a substrate or directly on the surface of the array. If polychromatic light, such as light reflected from a sample or a strip of a scene viewed from a spacecraft, passes through the variable filter and is spectrally resolved before incidence on the array, the output of all the elements in the array provides the spectral contents of the polychromatic light. High spectral resolving power is obtained by subtracting the output signals of adjacent elements in the array.

U.S. Pat. No. 5,166,755 mentions many applications. Non-imaging applications include measurement of spectral transmission through samples; for molecular absorption and emission spectra; for spectral reflectance measurements; for pollution and emission control by measuring transmission or absorption; for astronomical spectral analyses of stellar radiation; for pyrometry by measuring thermal radiation; and underwater spectrometry. Imaging applications include color copying machines; color printing; color facsimile machines; color picture-phone; color page scanning; robotic vision; aerial mapping; air-borne and space-borne resources monitoring; reconnaissance and surveillance; sorting of items; non-contact inspection; missile guidance; and star tracking.

It would be advantageous to have improved techniques for photosensing optical signals with ICs.

SUMMARY OF THE INVENTION

The invention provides various exemplary embodiments, including methods, apparatus, and systems. In general, the embodiments are implemented with integrated circuits that include photosensor arrays.

These and other features and advantages of exemplary embodiments of the invention are described below with reference to the accompanying drawings.

BRIEF DESCRIPTION OF THE DRAWINGS

FIG. 6 is a schematic cross-sectional view of another implementation of an assembly that can be used in FIG. 1.

FIG. 7 is a graph illustrating the laterally varying light transmission properties of a transmission structure in FIG. 6.

DETAILED DESCRIPTION

Figure 1:
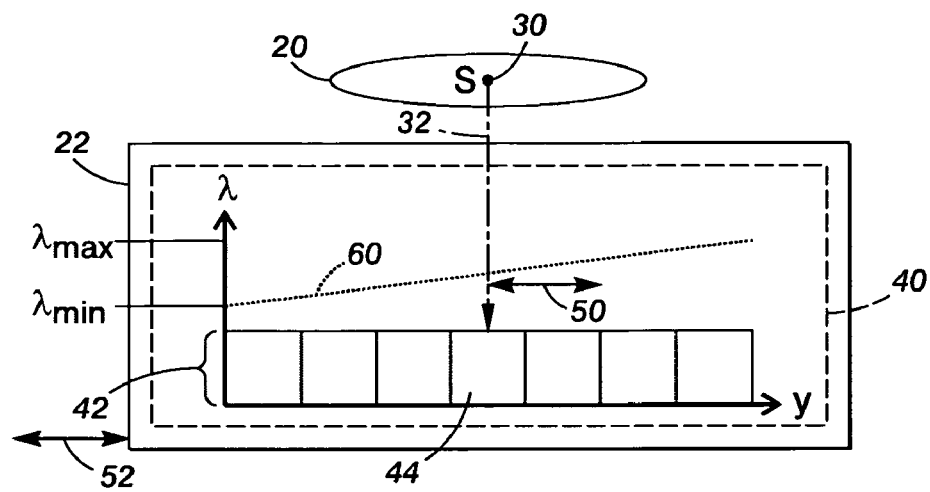
FIG. 1 is a schematic diagram illustrating relative scanning movement between an optical signal and a photosensor array in a sensing assembly.

In the following detailed description, numeric values and ranges are provided for various aspects of the implementations described. These values and ranges are to be treated as examples only, and are not intended to limit the scope of the claims. In addition, a number of materials are identified as suitable for various facets of the implementations. These materials are to be treated as exemplary, and are not intended to limit the scope of the claims.

"Light" refers herein to electromagnetic radiation of any wavelength or frequency; unless otherwise indicated, a specific value for light wavelength or frequency is that of light propagating through vacuum. The term "photon" refers herein to a quantum of light, and the term "photon energy" refers herein to the energy of a photon.

The various exemplary implementations described below address problems that arise in obtaining information about light. One of those problems is the difficulty of obtaining spectral information about an optical signal rapidly and without bulky, expensive equipment. Also, techniques in obtaining spectral information about a document or other two-dimensional object have poor spectral resolution.

The term "optical signal" is used herein to refer to a signal in the form of light. For example, an optical signal may "emanate from a point-like source", meaning that the light behaves as if its source were a point or had a very small area; for example, the light could be emitted or scattered by a particle or a compact group of particles. In contrast, a "line-like optical signal" is an optical signal that could be approximated by a straight line of point-like sources; illuminating a slit can produce a line-like optical signal, for example. A "two-dimensional optical signal" is an optical signal that could be approximated by a two-dimensional array of point-like sources; illuminating a two-dimensional object can produce a two-dimensional optical signal, for example.

Optical signals can also be described in terms of "spots", where a "spot" of an optical signal refers to an area of the signal that can be approximated by an optical signal emanating from a point-like source. If a line-like or two-dimensional optical signal is produced by illuminating a two-dimensional object, for example, a "spot" of the optical signal would emanate from a single position on the object's surface.

The term "sensing" is used herein in the most generic sense of obtaining information from a physical stimulus; sensing therefore includes actions such as detecting, measuring, and so forth. To "photosense" is to sense photons, and to "photosense quantity" of photons is to obtain information indicating a quantity of the photons. Photons that are photosensed are sometimes referred to herein as "incident photons".

A "photosensor" is used herein to refer generally to any element or combination of elements that senses photons, whether by photosensing quantity or any other information about the photons. A photosensor could, for example, provide an electrical signal or other signal that indicates sensed information, such as a signal indicating quantity of incident photons. If electrical sensing events occur in a photosensor in response to incident photons, the photosensor may integrate or otherwise accumulate the results of the electrical sensing events during a time period referred to herein as a "sensing period".

A "range of photon energies" or an "energy range" is a range of energy values that photons can have. An energy range can be described, for example, as a range of wavelengths or a range of frequencies or, in appropriate cases, by the range's central wavelength or frequency and possibly also the range's width. A "subrange" of a range of photon energies is a part of the range, and can be similarly described.

In general, each application of photosensing has a characteristic energy range, referred to as the "application's energy range", which is the range of photon energies over which it is necessary to obtain information in order that the application satisfies the relevant performance criteria. For example, if an application uses helium arc lamps, its energy range could encompass helium's major emission peaks.

In general, the upper and lower boundaries and widths of ranges and subranges are approximate. To photosense quantity of photons "throughout", "within", or "in" a range or subrange means to obtain information about quantity of photons that are predominantly within the range or subrange. In typical cases, between 60-90% of the sensed quantity of photons having energies within the range or subrange, but the percentage could be lower or higher. In some applications, 90% or even 95% or more of the sensed quantity of photons have energies within the range or subrange. Where an application requires that a minimum percentage or other proportion of sensed quantity of photons have energies within a range or subrange, the minimum percentage or other proportion is referred to herein as the "application's minimum photon proportion".

Some of the photosensing implementations described herein employ structures with one or more dimensions smaller than 1 mm, and various techniques have been proposed for producing such structures. In particular, some techniques for producing such structures are referred to as "microfabrication." Examples of microfabrication include various techniques for depositing materials such as growth of epitaxial material, sputter deposition, evaporation techniques, plating techniques, spin coating, printing, and other such techniques; techniques for patterning materials, such as etching or otherwise removing exposed regions of thin films through a photolithographically patterned resist layer or other patterned layer; techniques for polishing, planarizing, or otherwise modifying exposed surfaces of materials; and so forth.

In general, the structures, elements, and components described herein are supported on a "support structure" or "support surface", which terms are used herein to mean a structure or a structure's surface that can support other structures. More specifically, a support structure could be a "substrate", used herein to mean a support structure on a surface of which other structures can be formed or attached by microfabrication or similar processes.

The surface of a substrate or other support surface is treated herein as providing a directional orientation as follows: A direction away from the surface is "up", "over", or "above", while a direction toward the surface is "down", "under", or "below". The terms "upper" and "top" are typically applied to structures, components, or surfaces disposed away from the surface, while "lower" or "underlying" are applied to structures, components, or surfaces disposed toward the surface. In general, it should be understood that the above directional orientation is arbitrary and only for ease of description, and that a support structure or substrate may have any appropriate orientation.

An "integrated circuit" or "IC" is a structure with electrical components and connections produced by microfabrication or similar processes. An IC may, for example, be on or over a substrate on which it was produced or another suitable support structure. Other components could be on the same support structure with an IC, such as discrete components produced by other types of processes.

Implementations described herein include features characterized as "cells" and "arrays", terms that are used with related meanings: An "array" is an arrangement of "cells". An array on an IC or other support structure may also include circuitry that connects to electrical components within the cells such as to select cells or transfer signals to or from cells, and such circuitry is sometimes referred to herein as "array circuitry". In contrast, the term "peripheral circuitry" is used herein to refer to circuitry on the same support surface as an array and connected to its array circuitry but outside the array. The term "external circuitry" is more general, including not only peripheral circuitry but also any other circuitry that is outside a given cell or array.

Some of the implementations below are described in terms of "rows" and "columns", but these terms are interchangeable. Also, rows and columns are described herein as examples of "lines". Within an array, a "line" of cells refers herein to a series of cells through which a line can be drawn without crossing areas of cells that are not in the line. For example, in a two-dimensional array in which cells have uniform areas, a line of cells could be a row, a column, a diagonal, or another type of straight line; more generally, a line of cells could be straight or could include one or more non-straight features, such as curves or angles.

A "photosensor array" is an array in which some or all of the cells are or include photosensors. Accordingly, an IC "includes" a photosensor array if the IC includes an array of cells, and at least some of the cells include respective photosensors. A cell that includes a photosensor may also include "cell circuitry", such as circuitry that makes connections with the photosensor, that transfers signals to or from the photosensor, or that performs any other function other than photosensing. In general, a cell's photosensor and cell circuitry are within a bounded area of the array, an area sometimes referred to herein as the "cell's area". The part of a cell's area in which an incident photon can be photosensed is referred to herein as "sensing area".

In an application that includes a photosensor array, circuitry that "responds to" one or more photosensors can be any circuitry that, in operation, receives information from the photosensors about their photosensing results through an electrical connection. Circuitry that responds to a photosensor could be circuitry in the same cell as the photosensor, or it could be array circuitry, peripheral circuitry, or other external circuitry, or it could include any suitable combination of cell circuitry, array circuitry, peripheral circuitry, and other external circuitry.

Figure 2:
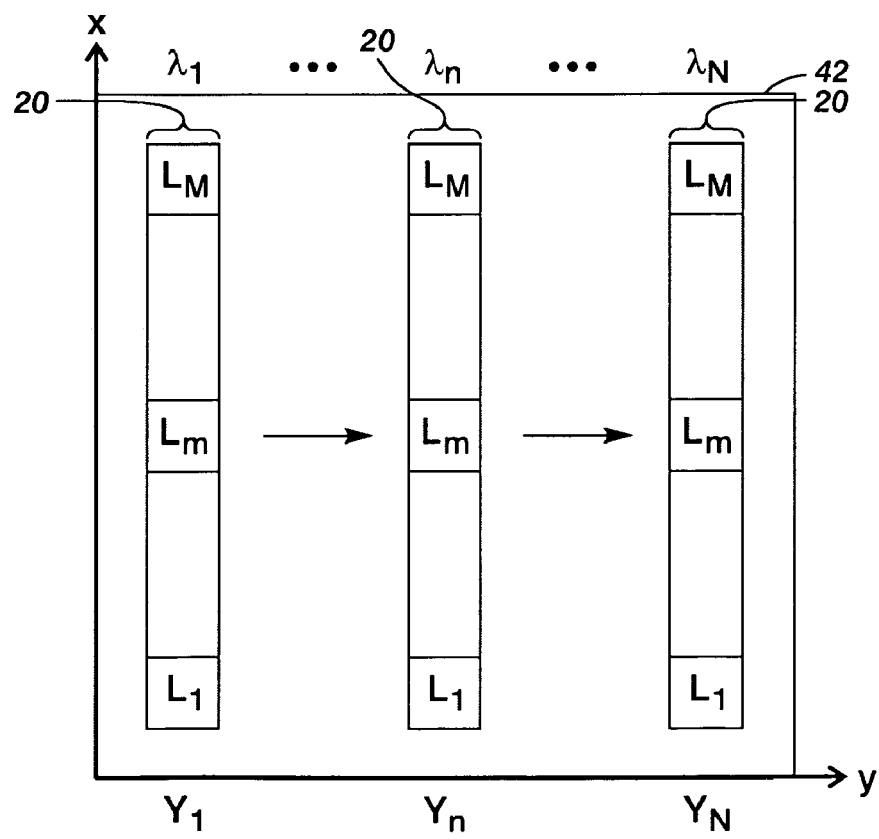
FIG. 2 is a schematic top view of a line-like optical signal in scanning movement relative to a photosensor array in FIG. 1.

FIGS. 1 and 2 illustrate general features of relative scanning movement. FIGS. 3-9 illustrate features of ICs and sensing assemblies that can be used as in FIGS. 1 and 2. "Relative movement" or "relative motion" occurs between an optical signal and a photosensor array when there is a change in the position at which at least one spot of the optical signal is incident on the array. For example, if the optical signal emanates from a point-like source such as a droplet or other such object, the optical signal includes only one spot and relative movement occurs if there is a change in the cells that photosense the center of intensity of the spot. Similarly, for a line-like optical signal, relative movement occurs if there is a change in the line of cells that photosense the spots of the signal. Also, for a two-dimensional optical signal, relative movement occurs if, for a spot of the optical signal, there is a change in the set of cells that photosense the spot. In general, relative motion between an optical signal and an array can result from motion of the array, motion of one or more of the components that provide the optical signal, or motion both of the array and of one or more of the components that provide the optical signal, and several examples are described below.

Sheets of paper are examples of "two-dimensional objects", meaning objects that have extent in at least two orthogonal directions. Other examples include biochips and well-plates, as mentioned below. In contrast to these other examples, a sheet of paper is also an example of a "sheet-like medium", meaning a two-dimensional object that is very thin in a third orthogonal direction, like a sheet, and that can be used as a medium for transfer of information.

The term "path" is used herein to refer to a substantially continuous series of positions at which a spot of light is incident, such as on a photosensor array during relative movement. A part of a path or other similar set of positions, such as a direction, is referred to herein as a "segment", and segments may overlap or be included one in another. Movement of a spot "along" a direction need not, however, follow a path, since the spot could jump from position to position along the direction.

"Relative scanning movement" or "relative scanning motion" between an optical signal and another component refers to relative movement in which a spot of the optical signal follows a path, such as a path across an array, across a two-dimensional object, or across an "optical component", meaning a component that interacts in some way with optical signals. For a point-like source, relative scanning movement of its optical signal follows a path across an array that is a line or a "line-like path", meaning a path across the array that approximates a line; for a line-like optical signal, relative scanning movement follows a set of paths across an array that includes a series of lines of cells that photosense spots of the signal; and relative scanning movement of a two-dimensional optical signal similarly follows a set of paths along which cells photosense spots of the signal. In each of these cases, the path or set of paths of spots of the optical signal is referred to as a "scan path".

In FIG. 1, light from optical signal 20 is incident on sensing assembly 22. Ray 32 illustratively represents light in optical signal 20 that is incident on assembly 22, with ray 32 representing a spot 30 designated "S". Within assembly 22, light from spot 30 is incident on IC 40, which includes photosensor array 42 with cell 44. Relative scanning movement between optical signal 20 and array 42 is illustrated by arrow 50, showing movement of ray 32 representing spot 30, and arrow 52, showing movement of assembly 22 including array 42.

Spot S can include a distribution of photon energies resulting, for example, from a light source (not shown), an illuminated object (not shown), an optional optical component (not shown) between the illuminated object and array 42, or any other component that participates in production of optical signal 20. Light sources, illuminated objects, and optical components can be implemented in many ways, some of which are described below. For example, potentially useful optical components include conventional imaging lenses (e.g. refractive lenses), diffractive optics (e.g. Fresnel lenses), various microlenses, and gradient index lenses (e.g. GRIN or Selfoc® lenses).

Array 42 can obtain information about the distribution of photon energies in spot S because its cells photosense subranges of photon energies that vary laterally in the y-direction as illustrated by curve 60. The range of photon energies photosensed by array 42 is illustratively bounded by minimum and maximum wavelengths $\lambda_{min}$ and $\lambda_{max}$, with curve 60 illustratively rising monotonically from $\lambda_{min}$ at the leftmost cell in array 42 to $\lambda_{max}$ at the rightmost cell in array 42, though the lateral variation could follow any appropriate function of position in the y-direction.

FIG. 2 shows in more detail relative scanning movement of optical signal 20 across a series of positions on array 42 that are in a scan path of optical signal 20. Optical signal 20 is illustratively a line-like optical signal extending in the x-direction, approximately perpendicular to its y-direction scan path across array 42, and is illustrated as including M discrete parts or locations $L_1$ through $L_M$, with each location $L_m$ being analogous to an image pixel; in the limiting case of M=1, optical signal 20 is a point-like optical signal that includes only one discrete location, $L_1$. In other cases described below, optical signal 20 can be two-dimensional, in which case it could be treated as a series of adjacent line-like optical signals each of which includes locations as shown in FIG. 2, extends in the x-direction, and moves across array 42 in the y-direction, like optical signal 20.

Locations $L_m$ are examples of spots of an optical signal, as defined above, and each of locations $L_m$ can be treated as containing a distribution $D_m$ of photon energies in a given implementation; the distributions for locations $L_1$ through $L_M$ can therefore be referred to as $D_1$ through $D_M$. The term "location" is used here because it suggests that the spots of the optical signal are located relative to each other. As mentioned below, various measures can be taken to preserve resolution of an optical signal so that its locations or other spots remain distinct and are located in the same way. As will be understood more fully from the below description of implementations with line-like or two-dimensional optical signals, it is advantageous to prevent the signal from spreading in the direction of relative movement, referred to generally herein as the y-direction; in other words, it is advantageous to keep the light of the optical signal concentrated such that each spot's light stays within the sensing area of a subrange cell.

Each of the locations $L_1$ through $L_M$ is photosensed at a series of N positions on array 42, illustrated as $Y_1$ through $Y_N$. At a given position along the y-direction, each column of cells of array 42 includes subrange cells that photosense the same subrange of photon energies, but at a given position along the x-direction, each row of array 42 includes subrange cells that vary laterally from photon energies with wavelength $\lambda_1$ through $\lambda_N$. In other words, at position $Y_n$, all M positions in optical signal 44 are photosensed in a subrange centered on $\lambda_n$. Similarly, in scanning between position $Y_1$ and $Y_N$, each distribution $D_m$ in optical signal 44 is photosensed in each of the subranges centered on $\lambda_1$ through $\lambda_N$.

Locations $L_m$ play an important role in the technique of FIGS. 1 and 2. The lower limit on size of locations $L_m$ constrains the resolution that can be obtained. In general, spatial resolution of locations $L_m$ is limited by the effective area of cells in array 42. For example, if optical signal 20 is an image of an object, optical components can be used to size up or down the image, increasing or decreasing spatial resolution respectively. Similarly, spectral resolution for each location $L_m$ depends on effective cell size in the y-direction and on the rate of change in $\lambda_n$ across array 42; for example, if variation in $\lambda_n$ results from variation in thickness of coating, as in some of the implementations described below, spectral variation depends on the gradient or steepness of the coating surface.

A signal indicates "spectral information" about photons if it indicates information about quantities of the photons with energies in each of a set of subranges of a range of photon energies. The spectral information could, for example, be a "spectral distribution" in which quantities in non-overlapping subranges are indicated. More specifically, a "complete spectral distribution" is a spectral distribution in which the subranges cover substantially all of an application's energy range.

Relative scanning movement across a photosensor array with laterally varying subrange cells as in FIGS. 1 and 2 makes it possible to obtain spectral information about optical signals. By choosing suitable materials in certain components, it is possible to obtain spectral information for the entire range from the deep ultraviolet to the far infrared or even for frequencies in the THz range.

Subranges of photosensing are "different from each other" in a given application if, at the application's minimum photon proportion, the subranges produce distinguishable photosensing results when the application requires. For example, if two subranges are so similar that their photosensing results cannot be distinguished when required, they are not different from each other. It should be noted, however, that subranges that are different from each other can nonetheless overlap or one of them can include another.

Figure 3:
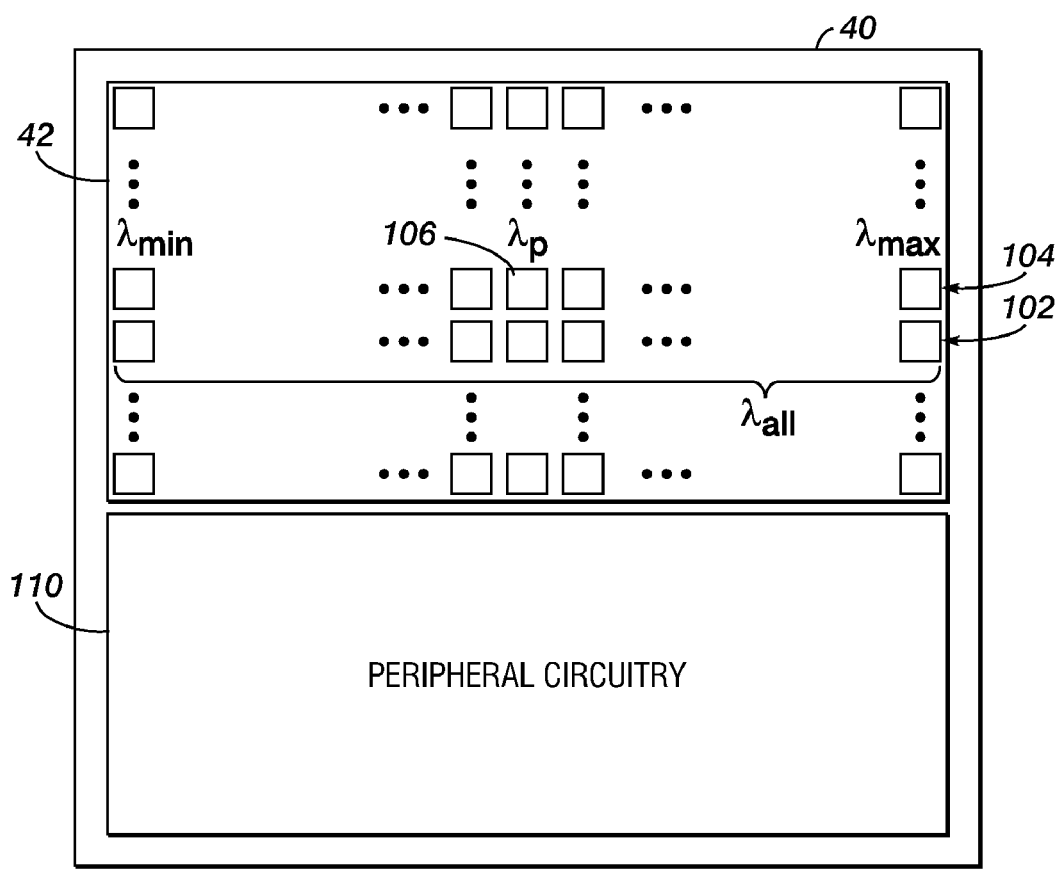
FIG. 3 is a schematic plan view of an implementation of an assembly that can be used in FIG. 1, including an integrated circuit (IC) with a photosensor array.

Assembly 22 in FIG. 1 can in general be implemented in any of the ways described below in relation to FIGS. 4-9. FIG. 3 is a schematic view of an exemplary implementation of IC 40 with photosensor array 42 that could be used in any of FIGS. 4-9. Photosensor array 42 is illustratively a two-dimensional array, with at least two rows of cells that include photosensors.

Different rows or other parts of photosensor array 42 can be provided with different coatings or can be otherwise structured so that their cells photosense different ranges or subranges of photon energies. As a result, the information obtained from a single IC can provide a detailed analysis of incident photons over a broad range of photon energies. In addition, reference cells, such as the cells in row 102, can be used to provide a spatially resolved real-time reference signal, such as to continuously monitor position of an optical signal as it follows a scan path across array 42.

Within an array, a "pair" of cells is any two cells; unless otherwise specified, the cells in a pair need not have any other specific relationship to each other. The cells in a pair are "near each other" if the distance between them meets a suitable criterion for nearness, such as being no greater than ten times the maximum diameter of the larger of the cells. In general, for example, two cells that are adjacent are also near each other. More generally, a set of cells are all "nearby" another cell if each cell in the set and the other cell, taken as a pair, are near each other. A feature of array 42 is that it includes one or more reference cells that are nearby to a subrange cell, such as by being adjacent to the subrange cell.

Each cell in row 102 photosenses photons throughout a suitable range, characterized as $\lambda_{all}$, to produce a reference for a nearby cell in row 104. For implementations in which it is advantageous to have signal strengths of the same order from a cell in row 102 and its paired cell in row 104, the cell in row 102 must be different from the cells in row 104. For example, it could have a different sensing area or it could have a gray filter coating different than a coating over the paired cell in row 104.

Each cell in row 104, on the other hand, photosenses a respective subrange between $\lambda_{min}$ and $\lambda_{max}$, with illustrative cell 106 photosensing a subrange centered around $\lambda_p$. IC 40 also includes array circuitry (not shown) as well as peripheral circuitry 110 which perform various functions relating to readout of photosensed information from array 42.

One advantage of the technique illustrated in FIG. 3 is that IC 40 provides a compact photosensor array that can be used within a system, such as with a scanning device. Results from more than one such IC within a system may be combined to obtain more complete spectral information. In general, photosensed quantities are "combined" when they are included together in any data structure or signal, possibly after one or more data processing or signal processing operations.

Figure 4:
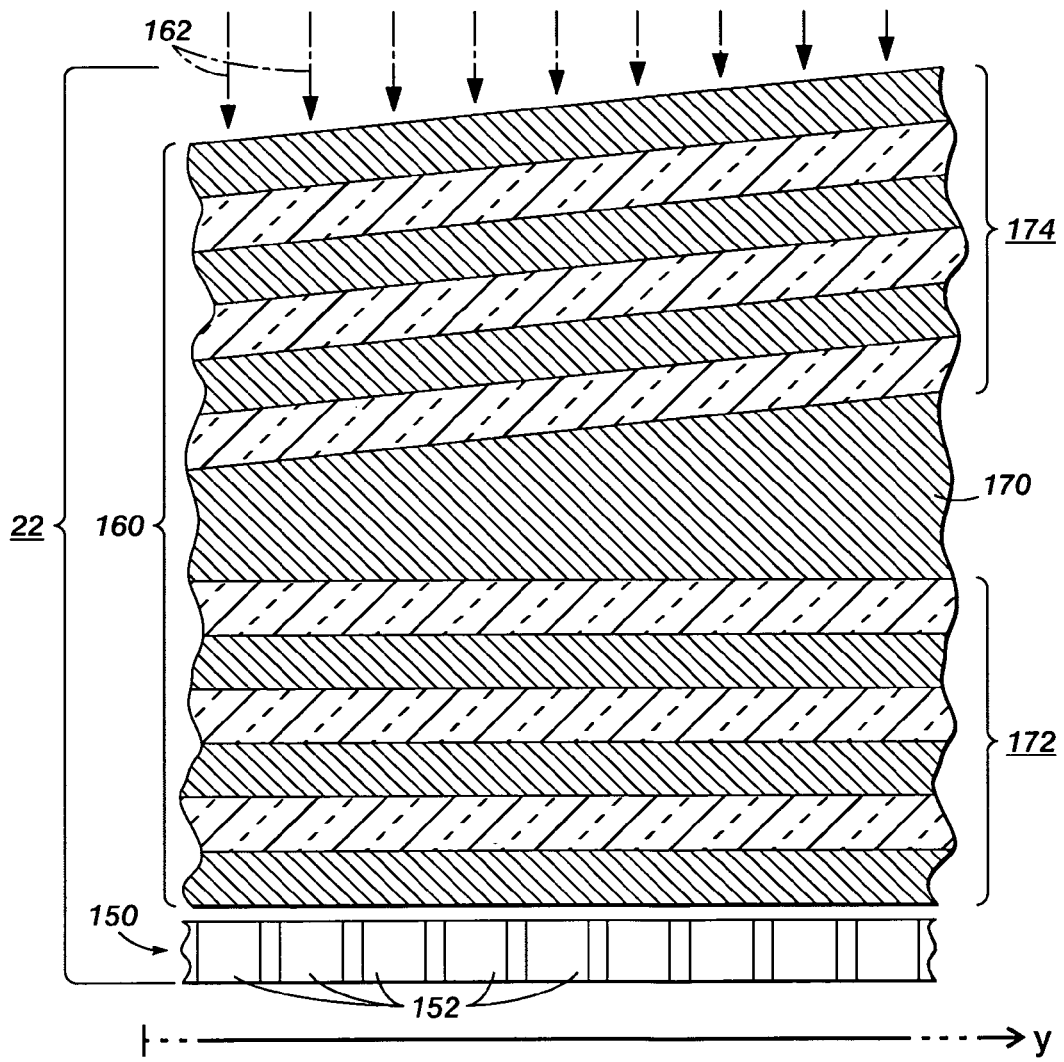
FIG. 4 is a schematic cross-sectional view of another implementation of an assembly that can be used in FIG. 1.

FIG. 4 illustrates an implementation of assembly 22, showing in greater detail how cells of an array photosense subranges, such as in row 104 in FIG. 3. As in other implementations described herein, assembly 22 in FIG. 4 can be supported by a suitable support component.

In FIG. 4, a cross-section has been taken through a fragment 150 of a photosensor array, with cells 152 of the fragment 150 shown schematically in cross-section. Over cells 152 is a transmission structure 160 that receives incident light 162, such as from any of the below-described implementations for obtaining an optical signal.

A structure that "transmits" photons, sometimes referred to herein as a "transmission structure", is any material structure through which light can propagate. It is not necessary that there be a one-to-one relationship between photons that enter a transmission structure and photons that exit from it as long as the structure provides exiting photons in response to entering photons as a result of light propagation through the structure.

More generally, to "transmit" photons is to perform a function by which exiting photons at an exit position are provided in response to entering photons at an entry position as a result of light propagation between the entry and exit positions. To "transmit only" a specified set of photons from a first position to a second refers to a function that transmits photons from the first position to the second, but predominantly photons in the specified set. As with photosensing, described above, if a transmission structure transmits only a specified set of photons, between 60-90% of the transmitted photons are in the specified set, but the percentage could be lower or higher. In some applications, 90% or even 95% or more of the photons are in the specified set.

One type of transmission structure is a "coating", meaning a layered structure of light-transmissive material that is on or over another component such as a photosensor array. A coating varies "continuously" along a scan path or other path if the coating varies as a continuous function of its position along the path.

A transmission structure provides (and a cell receives from a transmission structure) photons "throughout", "within", or "in" a range or subrange if the provided photons are predominantly within the range or subrange. As with photosensing, described above, between 60-90% of the photons from a transmission structure typically have energies within the range or subrange, but the percentage could be lower or higher. In some applications, 90% or even 95% or more of the photons have energies within the range or subrange.

Transmission structure 160 can, for example, be a film with laterally varying light transmission properties as described, for example, in co-pending U.S. patent application Ser. No. 10/922,870, entitled "Chip-size Wavelength Detector" and incorporated herein by reference in its entirety. In the portion of transmission structure 160 shown in FIG. 4, wedge-shaped transmissive cavity 170 is enclosed between reflective films 172 and 174, forming a wedge-shaped Fabry-Perot etalon. Because its thickness varies as a function of position along the y-axis, transmission structure 160 will transmit different wavelengths as a function of position along the y-axis.

Transmission structure 160 can be produced with appropriate coatings on or over a photosensor array. Films 172 and 174 and cavity 170 could all be produced, for example, by exposure to deposition beams in an evaporation chamber; films 172 and 174 with uniform thicknesses could be produced by appropriate on-axis deposition, while cavity 170 with laterally varying thickness can be produced by appropriate off-axis deposition. FIG. 4 illustratively shows films 172 and 174 as relatively thick compared to cavity 170, which would be appropriate for layers of non-metallic material such as $SiO_2$, $TiO_2$, or $Ta_2O_5$, with thicknesses designed as described below; such materials are typically used to produce Bragg mirrors by depositing thin alternating layers with low absorption coefficients and large differences in refractive indices. If films 172 and 174 are reflective metal, however, they could be much thinner.

For an implementation with non-metallic material, specific thicknesses of cavity 170 and films 172 and 174 could be designed from the desired transmitted wavelength $\lambda$ and the refractive index n of cavity 170. The thickness of cavity 170 is typically chosen to be $\lambda/(2n)$ or an integer multiple thereof, while the thicknesses of Bragg mirror layers within films 172 and 174 are typically $\lambda/(4n)$. The number of pairs of such layers in each of films 172 and 174 can vary between a few (e.g. 2-5) all the way up to 20 or 30, depending on the difference in refractive index between the two materials used, the desired transmission band width, and the desired stop band reflectivity. Therefore, in typical implementations, films 172 and 174 are much thicker than cavity 170, as suggested in FIG. 4.

Figure 5:
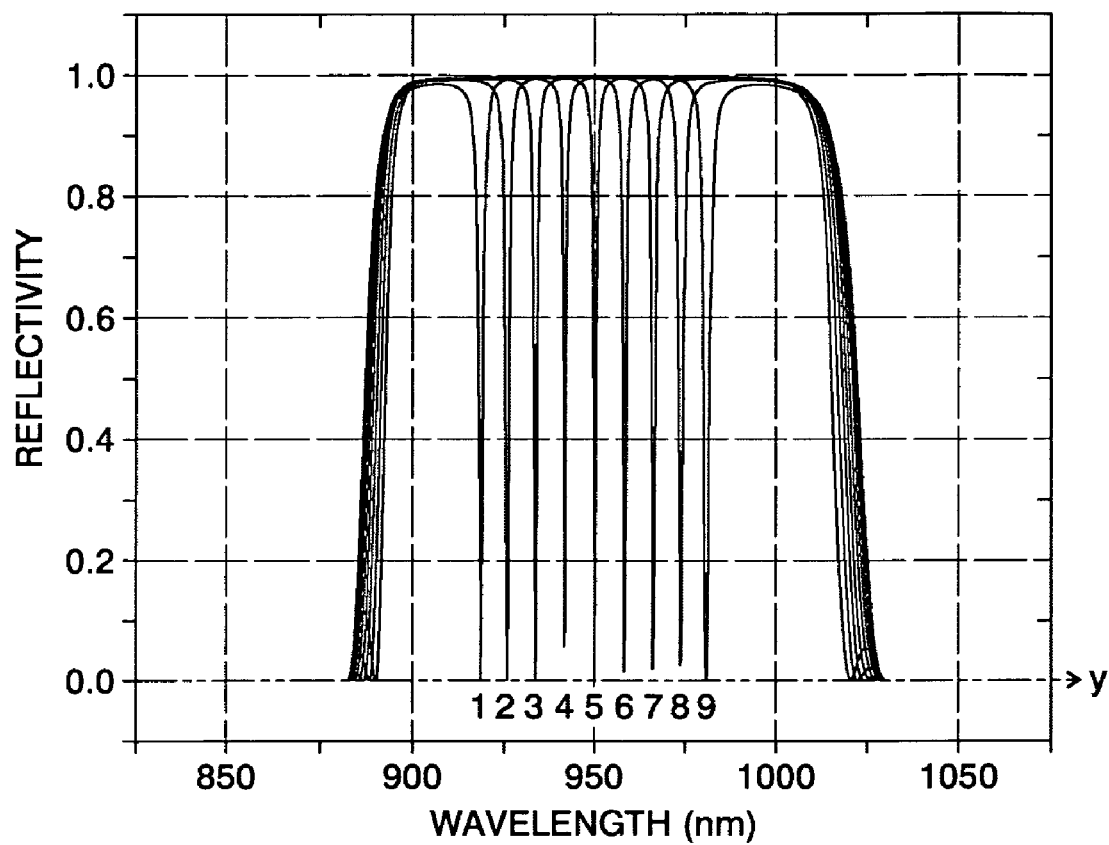
FIG. 5 is a graph illustrating laterally varying light transmission properties of a transmission structure in FIG. 4.

FIG. 5 illustrates the laterally varying light transmission properties of transmission structure 160. Because its thickness varies as a function of position along the y-axis, cavity 170 transmits different wavelengths as a function of position along the y-axis. Wavelengths of photons predominantly transmitted to nine of cells 152 as in fragment 150 are illustrated by the low reflectivity minima labeled 1 through 9. As can be seen, the high-transmissivity photon energy range for transmission structure 160 varies laterally.

FIG. 6 illustrates another implementation of assembly 22, with features that have the same reference numbers as in FIG. 4 being implemented as described above. Rather than transmission structure 160, however, assembly 22 includes transmission structure 180. Transmission structure 180 can, for example, be a laterally graded Bragg mirror in which each of layers 182, 184, 186, and 188 is laterally graded. Each of layers 182, 184, 186, and 188 could be produced as described above for cavity 170, using off-axis deposition in an evaporation chamber.

FIG. 7 illustrates the laterally varying light transmission properties of transmission structure 180. Because its thickness varies as a function of position along the y-axis, transmission structure 180 reflects different wavelengths as a function of position along the y-axis. Curves 200, 202, 204, and 206 are shown, representing reflectivity of the portion of transmission structure 180 over each of four cells 152 in fragment 150, with curve 200 being for the leftmost cell of the four in FIG. 6 and curve 206 being for the rightmost cell of the four. As can be seen, the high-reflectivity photon energy range for transmission structure 180 varies laterally.

Figure 8:
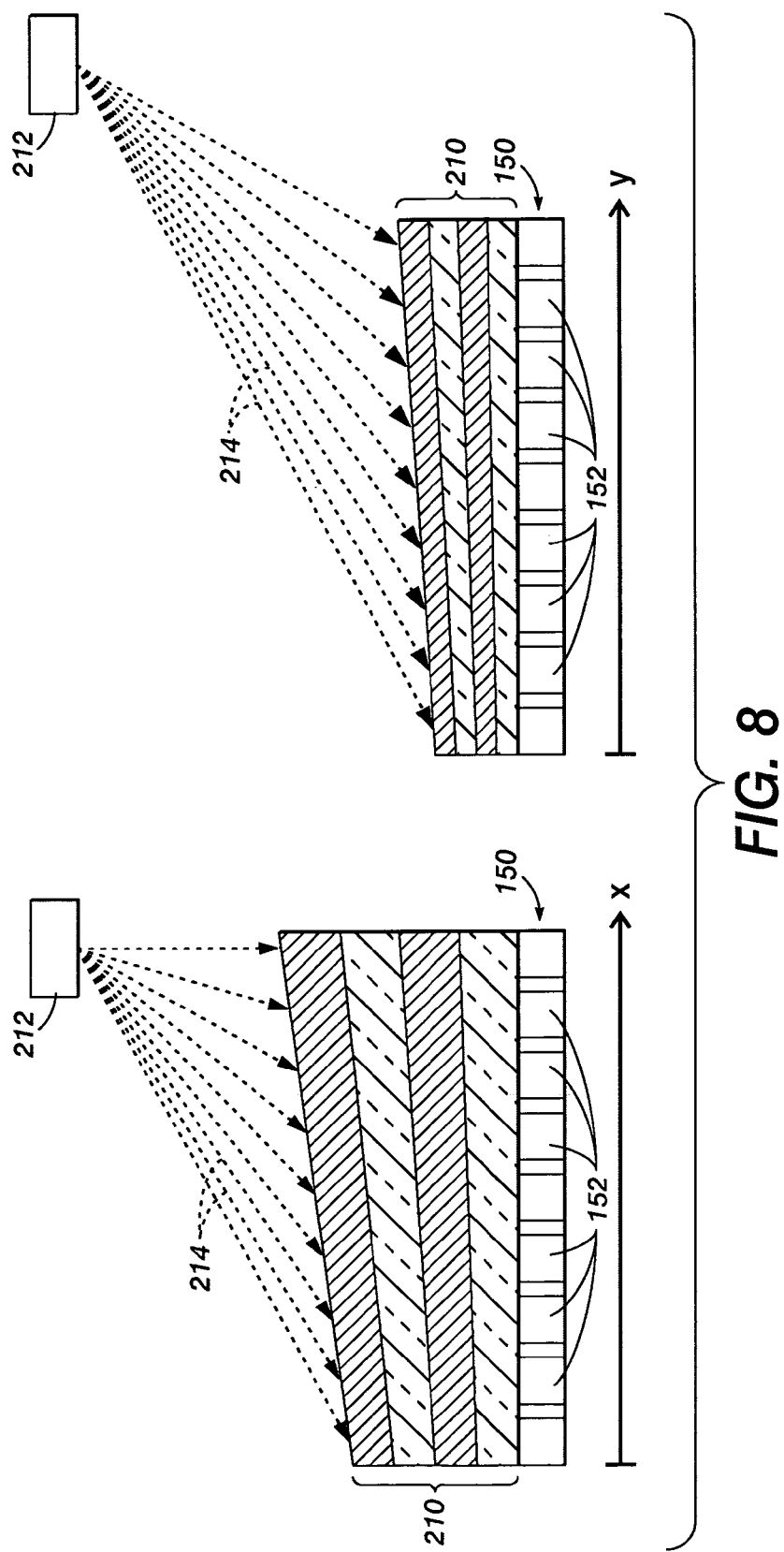
FIG. 8 illustrates a technique that produces a transmission structure that can be used in an assembly as in FIG. 1, showing orthogonal schematic cross-sectional views of deposition.

FIG. 8 illustrates a technique that produces transmission structure 210 with laterally varying light transmission properties similar to those illustrated in FIGS. 5 and 7 but with lateral variation in each of two dimensions. This technique can be used to produce different coatings for different rows of a photosensor array so that their cells photosense different ranges or subranges of photon energies, and can be used separately or in combination with reference cells.

Transmission structure 210 is produced on or over cells 152 of photosensor array 150 by using deposition source 212 to provide deposition beam 214 that can be characterized at any given point on the surface of structure 210 by two angles. One of the two angles results from angular variation of deposition beam 214 in the x-direction across array 150, while the other results from angular variation in the y-direction. As a result, the thickness gradient of structure 210 is similarly different in the x- and y-directions. Therefore, cells within each row extending in the y-direction will photosense a range of photon energies similarly to FIG. 7, but the range will be different than the range photosensed by cells in any other row extending in the same direction.

The technique of FIG. 8 could be implemented in a variety of ways. For example, during deposition, structure 210 could be formed on a support structure that is tilted as required, deposition source 212 could be tilted as required, or both kinds of tilt could be employed.

Figure 9:
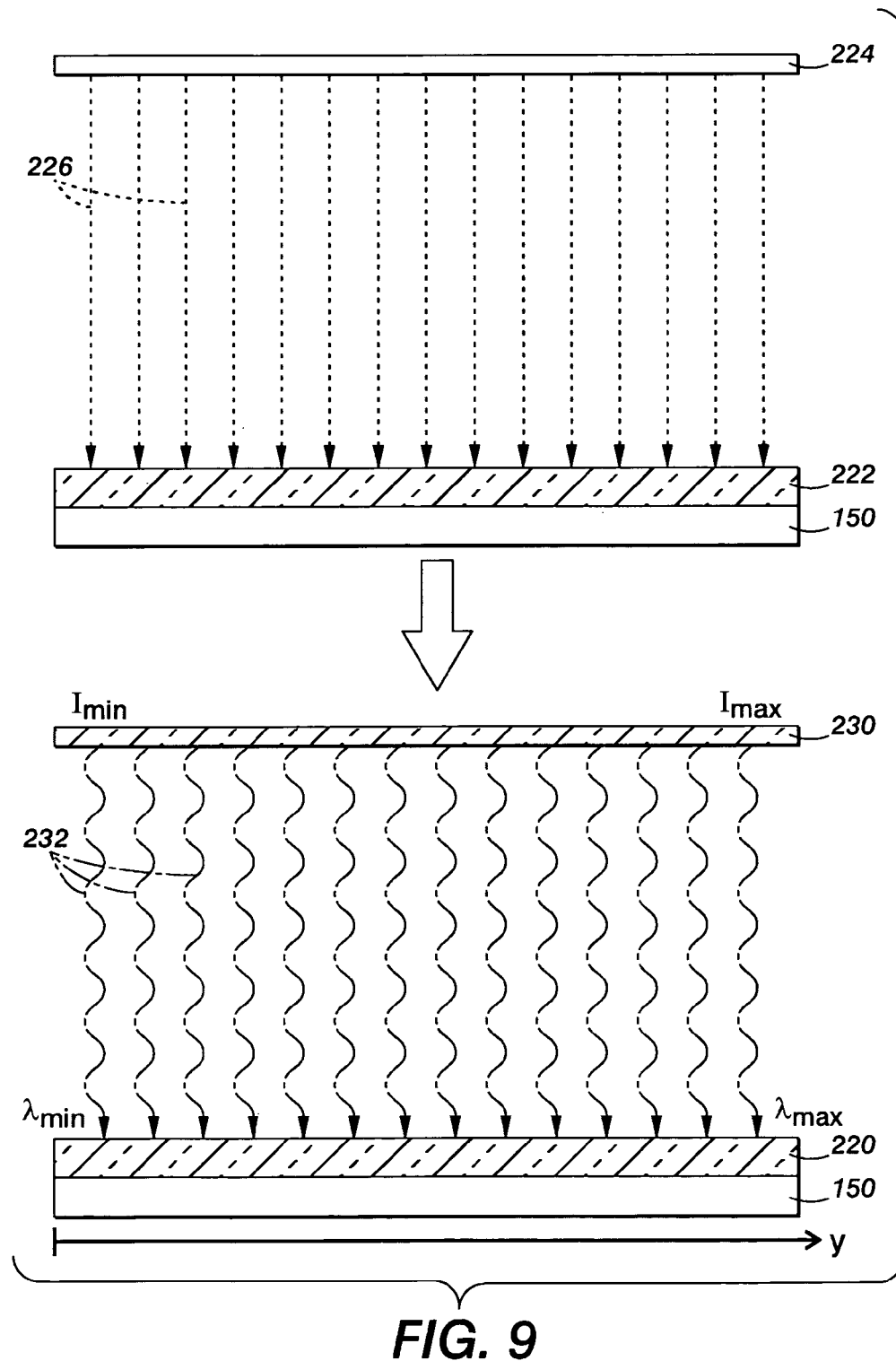
FIG. 9 illustrates another technique for producing a transmission structure that can be used in an assembly in FIG. 1, showing two schematic cross-sectional views of stages of the technique.

FIG. 9 illustrates a technique that produces transmission structure 220 with laterally varying light transmission properties similar to those illustrated in FIGS. 5 and 7 but without variation in thickness of transmission structure 220. The technique in FIG. 9 can be characterized as providing laterally varying optical thickness d*n, where d is thickness and n is index of refraction, but without actual variation in thickness d. In contrast, the techniques of FIGS. 4-8 provide varying optical thickness by providing actual variation in thickness.

In the upper part of FIG. 9, homogeneous coating 222 is deposited by deposition source 224, which provides deposition beam 226 uniformly over the surface of photosensor array 150 similar to those in FIGS. 4, 6, and 8. This operation could, for example, be implemented with conventional deposition techniques.

Then, in the lower part of FIG. 9, light source 230 provides radiation 232 that is scanned across the coating over array 150 to introduce a laterally varying change of refractive index in resulting transmission structure 220. For example, source 230 can be an ultraviolet source that provides intensity I with a constant value along each line parallel to the x-axis (perpendicular to the plane of FIG. 9), but varying from $I_{min}$ for lines nearer the x-axis to $I_{max}$ for lines farther from the x-axis, as shown in FIG. 9 by the values along the y-axis. As a result, the wavelengths transmitted to cells in array 150 can vary along the y-axis from $\lambda_{min}$ to $\lambda_{max}$, as shown. The same pattern of intensity can be concurrently applied by source 230 to each of a number of arrays that are appropriately arranged, allowing batch fabrication of arrays. Two-dimensional variation in optical density equivalent to that in FIG. 8 could also be obtained with two-dimensional variation in the ultraviolet source's intensity.

The techniques illustrated in FIGS. 4-9 could be implemented in various other ways, with different cells of a photosensor array photosensing slightly different subranges of a range of photon energies. For example, additional details about various production and calibration techniques and characteristics of transmission structures that could be employed are described in co-pending U.S. patent application Ser. No. 10/922,870, entitled "Chip-size Wavelength Detector" and incorporated herein by reference in its entirety. Also, co-pending U.S. patent application Ser. No. 11/316,241, filed Dec. 22, 2005, entitled "Transmitting Light with Photon Energy Information" and incorporated herein by reference, describes a step-like transmission structure that could be used.

If quantities photosensed by the cells are read out in parallel, spectral information about incident photons is obtained. As illustrated in FIG. 3, nearby cells, such as in a parallel row, can photosense quantities of photons throughout the range of photon energies to provide reference information. If adjacent cells in the array have overlapping subranges, computational techniques such as deconvolution can be used to improve accuracy.

In general, the resolution of a technique as in any of FIGS. 4-9 depends heavily on the number of cells in an array, the full width half maximum (FWHM) of the transmission peak, and the peak shift per cell. The smaller the FWHM and the peak shift, the better the resolution. On the other hand, the totally covered spectral width can be enhanced by increasing the FWHM and the peak shift per cell. Therefore, the technique can be customized to the needs of a specific application. For example, the use of a Fabry-Perot cavity as in FIG. 4 enables very high spectral resolution, while a version with multiple cavities and many layers as in commercially available products will be favorable for applications with low light intensities in combination with small spectral resolution such as with fluorescence. With such an approach, the spectral width of the transmission window and the reflectivity of the stop band can be optimized separately, which may be advantageous because the reflectivity of the stop band determines stray light suppression. It would also be possible to use a single laterally graded distributed Bragg reflector (DBR) mirror as in FIGS. 6 and 7 to obtain a photosensor array with high light sensitivity but limited wavelength resolution, appropriate for fluorescence or luminescence sensing.

In a version with only one DBR mirror with slightly graded transmission properties as in FIGS. 6-8, integrated over a photodiode array for example, the photocurrent in each cell is slightly different from its neighbors depending on the incident light spectrum. If the transmission properties of the DBR over each cell are known, the original spectrum of incident light can be reconstructed. The number of cells defines the number of spectral points that can be reconstructed and therefore determines spectral resolution. The reconstruction works best for wavelengths where transmission changes drastically from one cell to the next. Therefore, this technique could be used to resolve wavelengths at the edges of the DBR mirror. The DBR mirror could be positioned in such a way that the side edges on one side cover the spectral region being analyzed. Multiplication of the resulting photocurrent with a matrix that contains the transmission function of the DBR mirror provides a reconstruction of the incident light spectral distribution.

Resolution can be improved by positioning DBRs on a second row of the photodiode array so that the opposite edge of the reflectivity plateau overlaps the spectral range of interest. Once again, to evaluate the data, the total light intensity distribution must be known for all cells, which can be obtained from a third row of pixels without any DBRs.

A particular advantage of relative scanning movement as in FIGS. 1 and 2, when implemented with techniques similar to those of FIGS. 3-9, is that spectral information of a location or other spot of an optical signal can be collected step-by-step as the spot follows a scan path or is otherwise moved to different sets of cells, each of which obtains information about a respective subrange of photon energies. IC 40 can be thought of as a chip-size spectrometer that includes a photosensor array together with a laterally varying filter such as a coating. The laterally varying transmission and reflection properties of the coating over the photosensor array define a correlation between position and photon energy. Therefore the spatially dependent signal from the photosensor array contains information about the incident spectrum. Because of the distributed nature of the spectrometer and the fact that the incident light traverses the photosensor array in the process of resolving spectral distribution, sensitivity is improved, making additional optics unnecessary.

In general, high sensitivity is obtained by the above techniques because the light from the part of an optical signal is received at any given time by only a few cells with relatively narrow subranges. But by scanning light from a spot of the optical signal across the entire array, information about a complete range of photon energies can be obtained. This technique therefore allows longer integration times than conventional techniques but does not sacrifice throughput capacity.

Sensitivity can be adjusted by selecting the size and number of cells assigned to a specific subrange of photon energies. Simpler optics can be used and no dispersion element is necessary. Note that in conventional spectrometers, any light that is diffracted into the $0^{th}$, $2^{nd}$, and higher orders is wasted.

In experimental implementations, a coating as in FIG. 4 typically transmits approximately 60% of photons in its respective subrange. The subranges can be chosen with wavelengths that span between 0.01 and tens of nanometers (nm), depending on the design and gradient of the coating and the cell size of the photosensor array. Very high light yield can be achieved by using a highly sensitive photosensor, such as an avalanche photosensor array.

In contrast to transmission structures 160, 180, 210, and 220, any coating or other transmission structure over row 102 in FIG. 3 must function as a gray filter across the range $\lambda_{all}$ in order to provide a suitable reference. It may also be possible to leave row 102 uncoated in some implementations.

Techniques involving relative scanning movement and photosensing in subranges, as exemplified by the implementations in FIGS. 1-9, can be implemented in a many different ways for a wide variety of applications. For example, optical signal 20 could be obtained in many different ways, some of which are described below.

FIGS. 10-19 illustrate examples of how line-like and two-dimensional optical signals can be obtained from two-dimensional objects using various illumination techniques and optical components. Some of the illustrated techniques could also be used to obtain optical signals from point-like sources.

The term "object" is used herein in the general sense of any unitary thing from which light can emanate, whether through emission (e.g. radiation, fluorescence, incandescence, luminescence, etc.), scattering (e.g. reflection, deflection, diffraction, refraction, etc.), or transmission. The light "emanates from" or is simply "from" the object. Examples of objects that occur in implementations described below include sheets of paper, arrays of wells, biochips, etc.

Sheets of paper are examples of "two-dimensional objects", meaning objects that have extent in at least two orthogonal directions. Other examples include biochips and well-plates, as mentioned below. In contrast to these other examples, a sheet of paper is also an example of a "sheet-like medium", meaning a two-dimensional object that is very thin in a third orthogonal direction, like a sheet, and that can be used as a medium for transfer of information.

Figure 10:
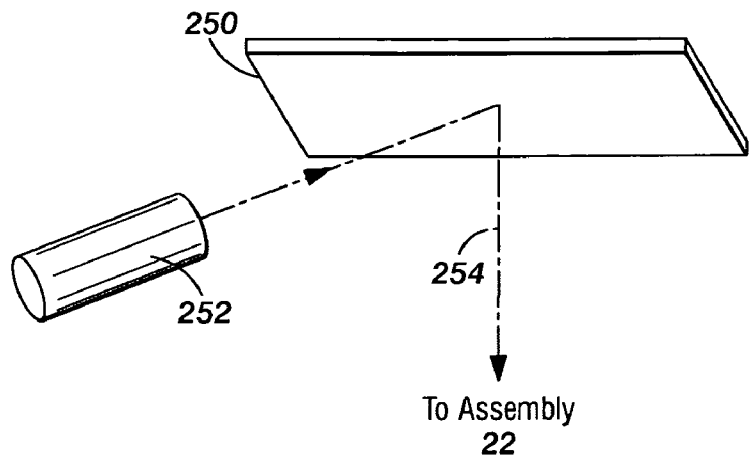
FIG. 10 is a schematic perspective view showing how a line-like optical signal could be obtained using a two-dimensional object such as a sheet of paper.
Figure 11:
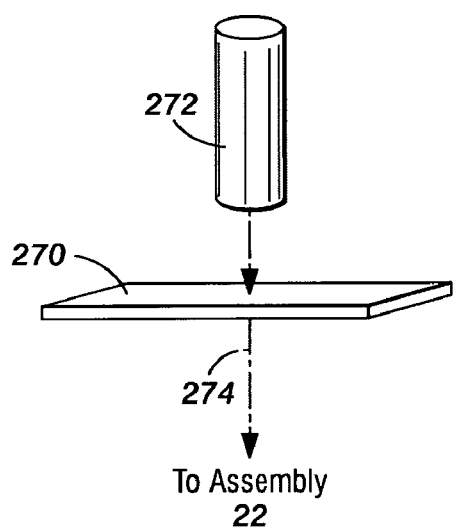
FIG. 11 is a schematic perspective view showing how a line-like optical signal could be obtained by illuminating a two-dimensional object such as a 96-well array.
Figure 12:
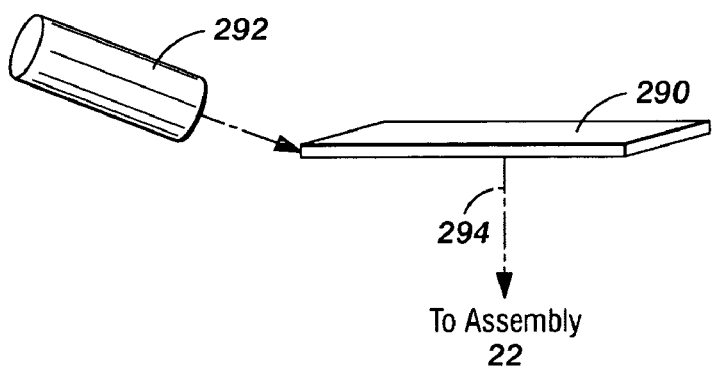
FIG. 12 is a schematic perspective view showing another way in which a line-like optical signal could be obtained by illuminating a two-dimensional object such as a biochip.

FIGS. 10-12 illustrate three implementations in which two-dimensional objects are illuminated in different ways to obtain optical signals. In each case, light from a source illuminates an object, resulting in the optical signal which may, for example, be a two-dimensional optical signal or a line-like optical signal as described in greater detail below. It would also be possible, of course, to use an optical signal that does not require illumination, such as an externally available image like that ordinarily captured by a camera or an optical signal that results from self-fluorescence or from a form of excitation other than illumination.

In FIG. 10, object 250 is illuminated by light from source 252, resulting in optical signal 254 due to reflection from object 250. For example, object 250 could be a sheet of paper or other sheet-like medium. More generally, object 250 could be any object with a two-dimensional surface that has varying reflectivity, such as a well-plate or a biochip, and optical signal 254 indicates reflectivity of the surface.

The term "biochip" is used herein to refer to any of various objects that have been developed for obtaining information about analytes optically. The analytes could be contained, for example, in a layer of fluid or in fluid contained within a channel.

The term "fluid" is used herein to encompass liquids, gasses, and aerosols. The terms "layer" and "channel" are used herein with slightly different meanings: A "layer" of fluid is any thin liquid or aerosol layer that is captured within a carrier structure; for example, a glass slide's surface could hold a layer of fluid that contains analytes, and the fluid could in turn be covered by another glass slide or the like so that it is captured by surface tension effects. In contrast, a "channel" is any tube or other enclosed passage that can contain fluid; for example, a channel can be defined in a "fluidic structure", meaning a structure that depends for its operation on fluid positioning or fluid flow.

In FIG. 11, object 270 is illuminated or backlit by light from source 272, resulting in optical signal 274. In this configuration, optical signal 274 results from transmission of light through object 270. Therefore, this configuration is appropriate for a well-plate, a biochip, or another two-dimensional object in which absorption, internal reflection, or another characteristic that affects light transmission varies from position to position. Optical signal 274 can therefore indicate absorption or internal reflection characteristics of object 270.

In FIG. 12, object 290 is a waveguiding structure in which photons can emanate in response to illumination or other excitation, such as light from source 292. Object 290 could, for example, be a biochip with fluid within or adjacent to waveguides or with non-fluid particles adjacent to waveguides. In response to illumination or other excitation, analytes or other particles within object 290 fluoresce, providing optical signal 294. Optical signal 294 therefore indicates differences between fluorescence spectra at different positions within object 290.

Various biochips and other two-dimensional objects can be implemented with illumination or other excitation techniques that cause fluorescence. One such technique, for example, is enhanced light-target interaction, which can be accomplished by anti-resonant waveguide techniques or other suitable excitation techniques. Enhanced light-target interaction is especially important in characterizing single particles or low concentrations of biological or chemical agents. In general, an anti-resonant waveguide has a core region surrounded by a cladding layer with a higher refractive index than the core region. Where the core region is a fluid that contains an analyte, light can be guided within the fluid, permitting photonic interaction over an extended length.

Anti-resonant waveguide techniques are described in greater detail in co-pending U.S. patent application Ser. No. 10/976,434, entitled "Anti-resonant Waveguide Sensors" and incorporated herein by reference in its entirety. Additional techniques are described in Goddard, N. J., Singh, K., Bounaira, F., Holmes, R. J., Baldock, S. J., Pickering, L. W., Fielden, P. R., and Snook, R. D., "Anti-Resonant Reflecting Optical Waveguides (ARROWs) as Optimal Optical Detectors for MicroTAS Applications", dias.umist.ac.uk/NJG/Abstracts/MicroTAS/MicroTas2.htm, pp. 1-5, and Singh, K., and Goddard, N. J., "Leaky Arrow Waveguides for Optical Chemical and Biosensors", (Abstract Submitted to Biosensors 1998), dias.umist.ac.uk/NJG/Abstracts/Biosensors/ARROW-Biosensors.htm, pp. 1-2, both of which are incorporated herein by reference.

In optical biosensors, the interaction between light and target molecules is typically very weak. Anti-resonant waveguide techniques can improve the interaction because of the extended length in which interaction occurs. More particularly, in contrast to excitation techniques that use evanescent fields of ordinary waveguides and therefore require very small channels, fluidic channels with maximum transverse dimensions as great as a few millimeters can be used as anti-resonant waveguides. Suitable configurations can include, for example, an aerosol in a glass capillary tube or a liquid film between glass slides. The excitation could be with visible light, ultraviolet light, infrared light, radiation in the terahertz range, or any other appropriate electromagnetic radiation. Examples of specific sensing components employing anti-resonant waveguide techniques are described in greater detail in co-pending U.S. patent application Ser. No. 11/316,660, filed Dec. 22, 2005. entitled "Providing Light To Channels Or Portions" and incorporated herein by reference in its entirety.

In the specific example of FIG. 12, in response to light from source 292, an analyte within object 290 fluoresces, emitting light with a characteristic spectrum of photon energies. A portion of the light is emitted toward assembly 22, becoming part of optical signal 294. After possibly passing through an optical component, photons can therefore be photosensed by cells of photosensor array 42 on IC 40.

In each case in FIGS. 10-12, the resulting optical signals 254, 274, and 294 could be provided thus to assembly 22 through an optical component (not shown), which, as described above, may not be necessary in some implementations. FIGS. 13-19 illustrate several specific configurations that each include an example of an optical component.

In all the implementations illustrated in FIGS. 13-19, relative scanning movement must occur between the optical signal and the photosensor array as described above in order to collect photon energy information in all subranges across the array, and this is sometimes referred to below as the "first relative scanning movement" or "primary relative scanning movement." In addition, relative scanning movement is necessary in some implementations to obtain photon energy information about all parts or spots of an object, and this scanning movement is sometimes referred to herein as "second relative scanning movement" or "secondary relative scanning movement." In some implementations, as in FIGS. 16-19, both primary and secondary relative scanning movement can be obtained by operating a single scanning device, but two scanning devices are required in other implementations. Several specific scanning implementations are discussed in greater detail below in relation to FIGS. 21-23.

Figure 13:
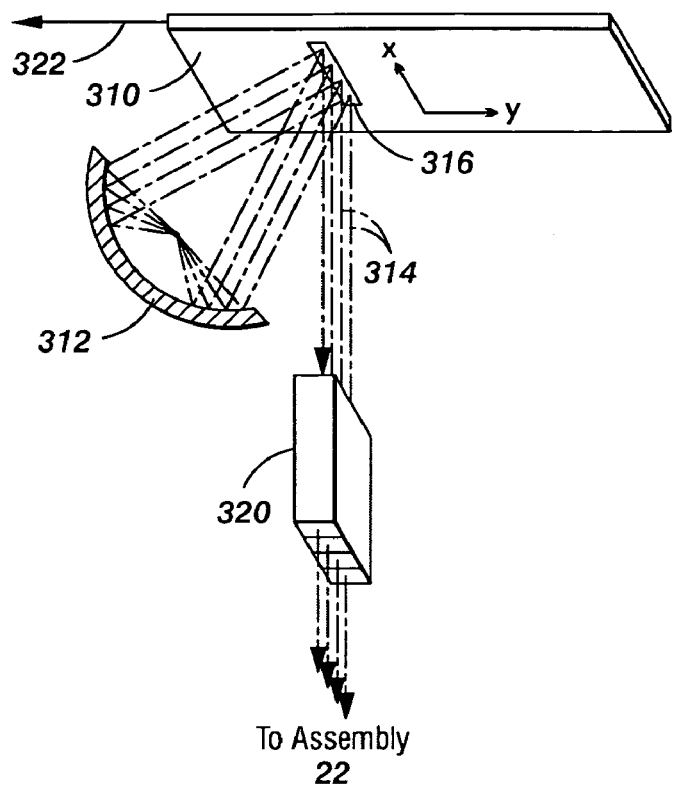
FIG. 13 is a schematic perspective view illustrating an illumination technique and an optical component that can be used to obtain a line-like optical signal.
Figure 14:
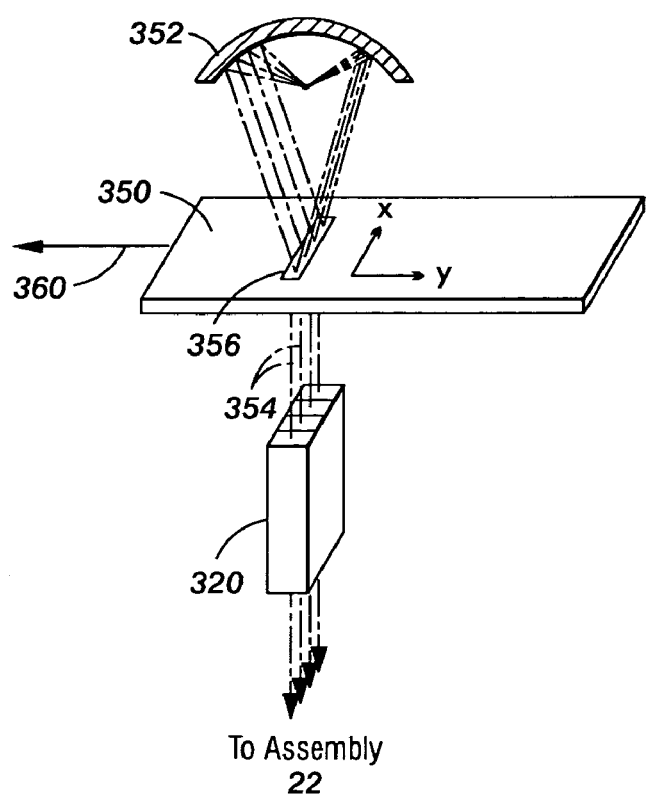
FIG. 14 is a schematic perspective view illustrating an alternative combination of an illumination technique with an optical component to obtain a line-like optical signal.

In FIGS. 13 and 14, a two-dimensional object is illuminated with a very thin line, and secondary relative scanning movement can be performed between the illumination and the object to obtain optical signals from all parts of the object; in these examples, the thickness of the illuminating line determines the spatial resolution in a y-direction, while an optical component preserves resolution in an x-direction. In FIGS. 15-19, in contrast, a two-dimensional optical signal is received from the object, and an optical component converts it to a line-like optical signal or to a two-dimensional optical signal that can be scanned across a photosensor array in assembly 22.

Illumination and optical techniques to obtain line-like optical signals, examples of which are described below in relation to FIGS. 13-15, generally fall into either of two basic possibilities. One of these possibilities uses "line-like illumination", meaning illumination approximating a line, while the other uses a "line-like aperture", meaning an aperture approximating a line.

In the first possibility, the size of an illuminated field defines the size of the resulting optical signal and an optical component preserves resolution in the direction of the line; for example, to obtain a line-like optical signal extending in an x-direction in an x-y plane, an illuminated field can be illuminated with a line-like illumination. A very thin line of illumination may be necessary to obtain a desired spatial resolution in the y-direction while an optical component preserves resolution in the x-direction. A secondary scanning device can be used to produce relative movement between a combination of illumination and optical components and an object being illuminated in order to cover the whole object.

In the second possibility, an illuminated field is larger than the desired optical signal, such as when a complete two-dimensional object is illuminated, and an optical component provides both a line-like aperture, such as an aperture defining a very thin line, and a structure that preserves resolution in the x-direction. Here again, a secondary scanning device can produce relative movement, in this case either between the illuminated field and an optical component or between the illuminated object and a combination of illumination and optical components.

As described below in relation to FIGS. 16-19, techniques to obtain two-dimensional optical signals by illuminating two-dimensional objects generally use a lens or lens-like optical component to preserve resolution in both x- and y-directions. The optical components can be used to image the illuminated object onto a two-dimensional photosensor array. At a given time, each specific illuminated location in the y-direction of the object is imaged onto a specific location in the y-direction of the array. This enables concurrent photosensing of different locations in different energy subranges. Primary relative scanning movement can be obtained by moving the object in approximately the y-direction relative to a combination of illumination, optical, and sensing components, enabling photosensing of a series of subranges for each location as in FIG. 2.

FIG. 13 illustrates an example in which sheet 310 of paper or another suitable sheet-like medium bears an image on its lower side and is illuminated from its lower side by source 312, which could, for example, be a white LED array with appropriate optics. In order to produce a line-like optical signal 314 similar to optical signal 20 in FIG. 2, a line-like segment 316 of sheet 310 is illuminated. Line-like optical signal 314 is then transmitted through an optical component such as Selfoc® lens array 320 to preserve resolution in the x-direction. From array 320, the optical signal can be transmitted to assembly 22. To obtain a complete image of sheet 310, a series of line-like optical signals similar to signal 314 must be obtained, such as by secondary relative scanning movement or other relative movement between source 312 and sheet 310, as suggested by arrow 322. Examples of relative scanning movement between optical signals like signal 314 and sensing assemblies are described below for several applications.

Similarly, FIG. 14 illustrates an example showing object 350, which can be an array that presents results of biological or chemical analysis in optical form, such as a 96-well-plate for analyzing biological or chemical samples. Object 350 could be illuminated from its backside by source 352, as shown, or alternatively could be illuminated from its front side as described above in relation to FIG. 13. In either case, a line-like optical signal 354 can be produced from a line-like segment 356 of plate 350. As in FIG. 13, signal 354 is transmitted through Selfoc® lens array 320 and thence to assembly 22. Also, as in FIG. 13, a complete image can be obtained, such as by secondary relative scanning movement or other relative movement between source 352 and object 350, as suggested by arrow 360.

Figure 15:
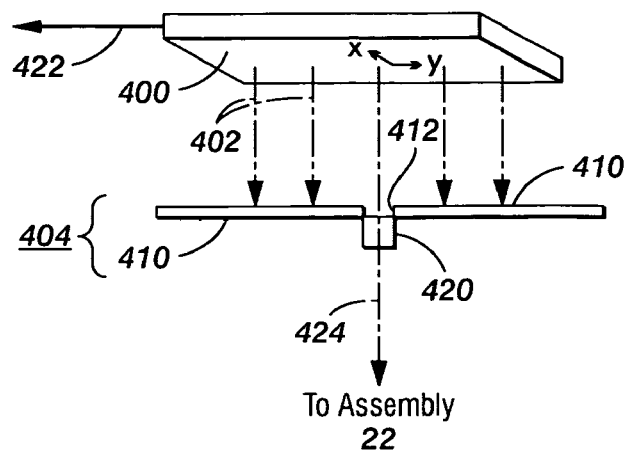
FIG. 15 is a schematic partially perspective view illustrating an optical component that can be used to obtain a line-like optical signal from a two-dimensional optical signal.

FIG. 15 illustrates an example in which object 400 is illuminated in any of the ways described above in relation to FIGS. 10-12, providing two-dimensional optical signal 402. In this implementation, optical component 404 illustratively includes both a two-dimensional light-blocking layer 410 with slit 412, and also Selfoc® lens array 420, similar to array 320 in FIGS. 13 and 14. As in the above implementations, relative scanning movement or other relative movement between object 400 and component 404, as suggested by arrow 422, results in a series of line-like optical signals 424, each extending in the x-direction, with array 420 preserving resolution in the x-direction.

The techniques illustrated in FIGS. 13-15 could also be implemented to obtain optical signals that emanate from a point-like source. For example, in FIGS. 13 and 14, illumination could be provided to one location of an object at a time. Similarly, in FIG. 15, slit 412 could be the size of one location rather than a line.

Figure 16:
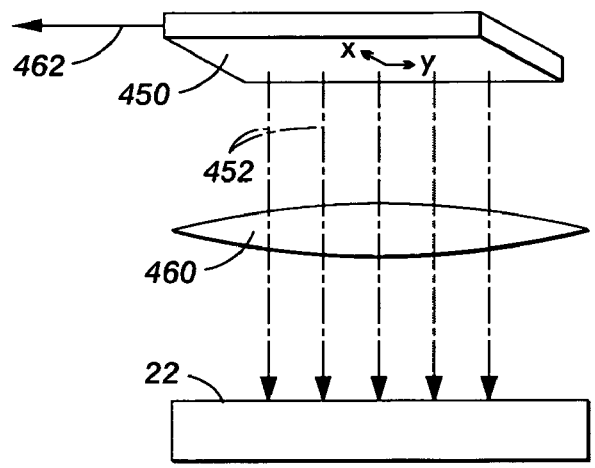
FIG. 16 is a schematic partially perspective view illustrating an optical component that can be used to focus a two-dimensional optical signal on a sensing assembly as in FIG. 2.

In FIG. 16, object 450 is illuminated to produce two-dimensional optical signal 452. An optical component is implemented in this case as a conventional lens 460 and is positioned such that it produces a sharp image of illuminated object 450 on photosensor array 42 in assembly 22. In other words, light in optical signal 452 is focused so that individual illuminated locations of object 450 are photosensed at respective locations of array 42, resulting in photosensing different energy subranges at different locations. Object 450 can be imaged one-to-one onto array 42 by positioning both object 450 and array 42 at twice the focal length of lens 460. Similarly, one could use optical components to produce larger or smaller images of object 450, resulting in higher or lower resolution and the necessity of a larger or smaller array 42, respectively.

Figure 17:
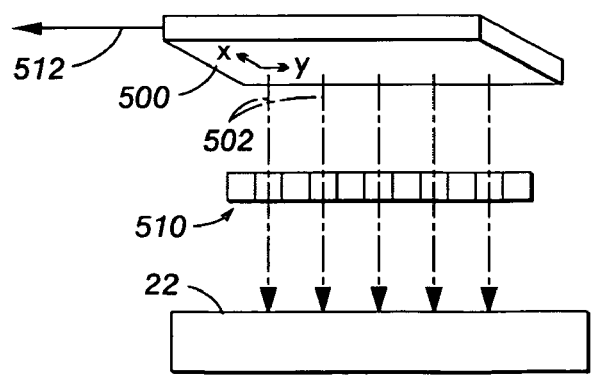
FIG. 17 is a schematic partially perspective view illustrating an alternative optical component that can be used in place of the optical component in FIG. 16.

To avoid failures during the imaging process, a conventional lens like lens 460 would ordinarily have to be bigger than the object being imaged. Replacing lens 460 by a Selfoc® or GRIN lens avoids this problem. In FIG. 17, object 500 is illuminated to produce two-dimensional optical signal 502. In this case, however, an optical component is implemented as a two-dimensional Selfoc® lens array 510, producing approximately the same optical result described above in relation to FIG. 16.

Figure 18:
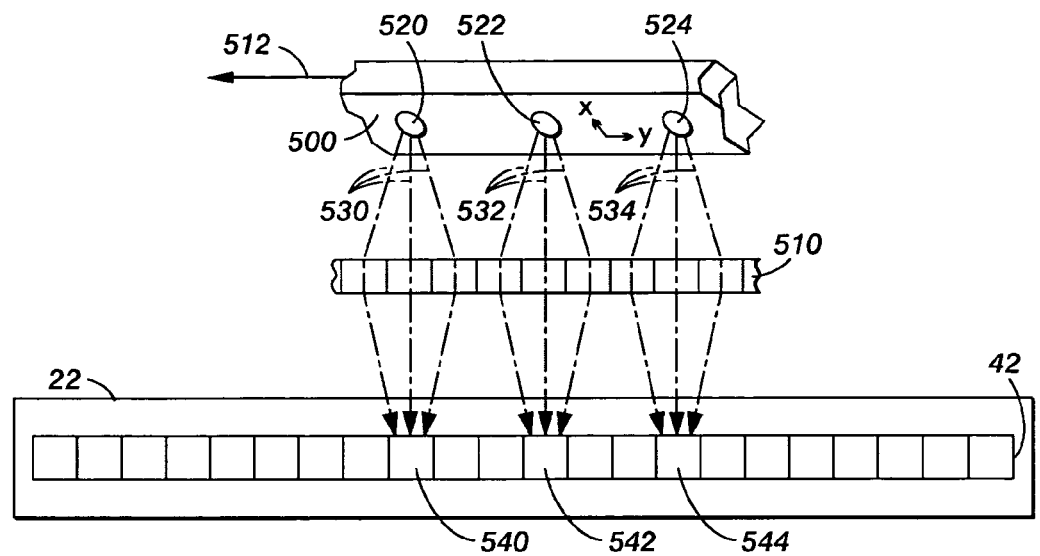
FIG. 18 is a schematic partially perspective view illustrating in greater detail an implementation of the technique in FIG. 17.

FIG. 18 shows a detail from one implementation as in FIG. 17, with similar components having the same reference numerals. As in FIG. 17, object 500 is illuminated to produce a two-dimensional optical signal. Two-dimensional Selfoc® lens array 510 images object 500 onto array 42 in sensing assembly 22.

As object 500 moves as shown by arrow 512, specific locations 520, 522, and 524 move through the illuminated field. Locations 520, 522, and 524 emanate photons, represented respectively by ray groups 530, 532, and 534; for example, the photons may result from reflection, transmission, or fluorescence. When incident on array 42, ray groups 530, 532, and 534 are photosensed by cells 540, 542, and 544, respectively. As explained below in relation to FIG. 20, quantities read out from cells of array 42 can be used to obtain spectral information about locations 520, 522, and 524 even though all three locations are concurrently traveling past array 42.

Figure 19:
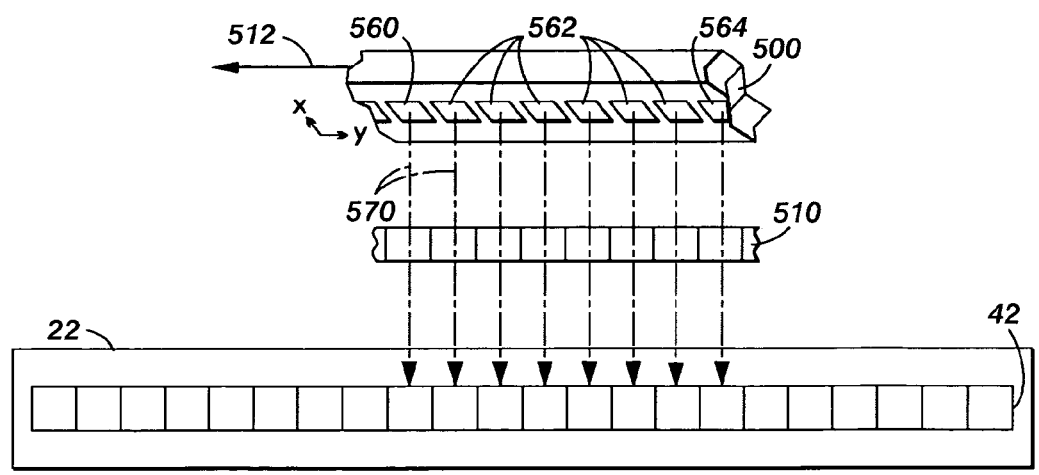
FIG. 19 is a schematic partially perspective view illustrating in greater detail another implementation of the technique in FIG. 17.

FIG. 19 shows an alternative to the implementation in FIG. 18, with similar components again having the same reference numerals. In this case, object 500 includes a continuous sequence of closely spaced locations moving through the illuminated field.

FIG. 19 shows a group of the locations passing through the illuminated field, led by location 560, after which follow several intermediate locations 562 and, finally, location 564. Locations 560, 562, and 564 emanate photons, represented by rays 570, such as by reflection, transmission, or fluorescence, and the photons pass through Selfoc® lens array 510 so that, for each of locations 560, 562, and 564, emanating photons are predominantly incident on a different cell of array 42 than photons emanating from other nearby locations. As in FIG. 18, quantities read out from cells of array 42 can be used to obtain spectral information about locations 560, 562, and 564 even though a continuous sequence of closely spaced locations is concurrently traveling past array 42.

Various other illumination schemes and optical components could be used to provide point-like, line-like or two-dimensional optical signals that can be scanned across array 42. As can be understood from the below description, the nature of the optical signal received by assembly 22 will affect the choice of techniques for reading out information about sensed quantities of photons in different subranges of the spectrum.

Figure 20:
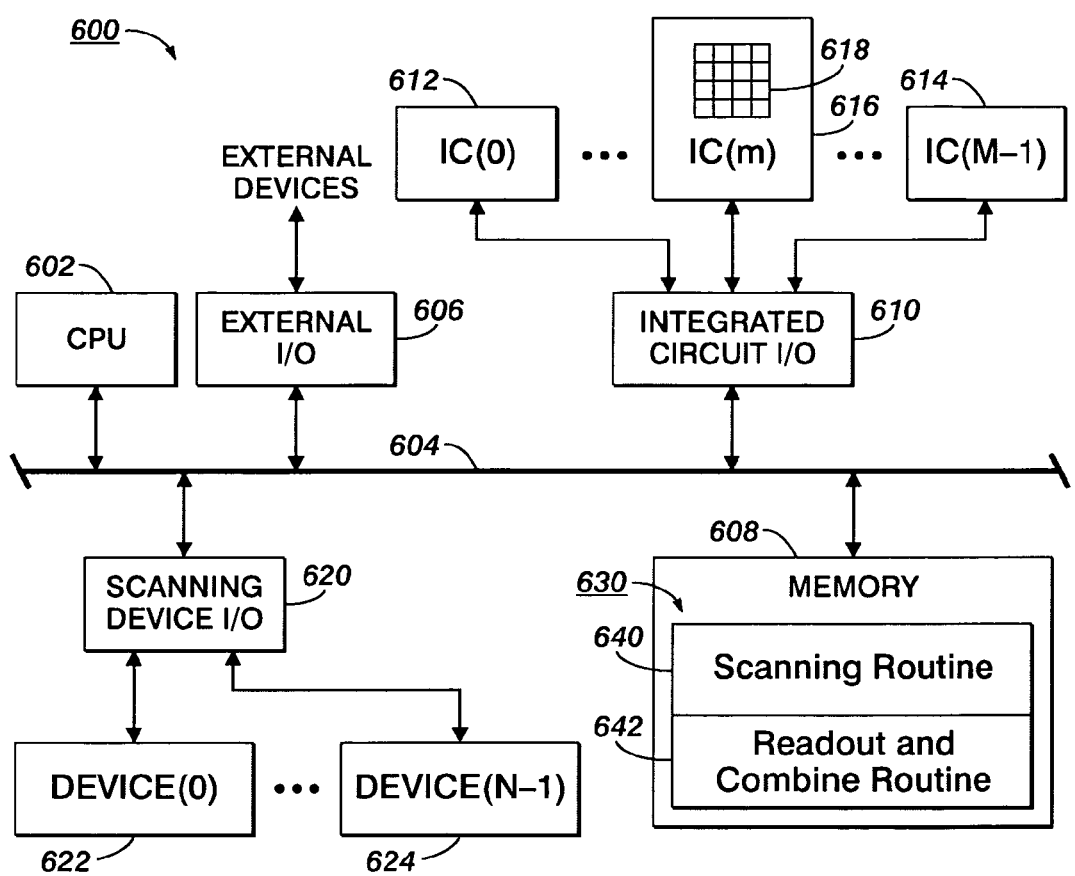
FIG. 20 is a schematic block diagram of a system that could control relative scanning movement as in FIG. 1.

FIG. 20 illustrates features of a system in which relative scanning motion occurs. In FIG. 20, system 600 is an exemplary system that could be used to obtain spectral information using photosensing with relative scanning movement as described above. System 600 illustratively includes central processing unit (CPU) 602 connected to various components through bus 604, but a wide variety of other architectures could be employed, including any appropriate combination of hardware and software, as well as specialized hardware components such as application specific integrated circuits (ASICs) for one or more of the illustrated components or in place of a software component executed by CPU 602.

System 600 also includes external input/output (I/O) component 606 and memory 608, both connected to bus 604. External I/O 606 permits CPU 602 to communicate with devices outside of system 600. For interactive applications, external I/O 606 could be connected to a suitable user interface, such as a monitor and keyboard (not shown). Additional components connected to bus 604 are within or connected to system 600. In the illustrated implementation of system 600, IC I/O 610 is a component that permits CPU 602 to communicate with one or more ICs in sensing assembly 22. M ICs are illustrated by a series from IC(0) 612 to IC(M-1) 614, including IC(m) 616 with a photosensor array 618. Similarly, scanning device I/O 620 is a component permitting CPU 602 to communicate with various devices to produce relative scanning movement, such as motors and sensors; N scanning devices are represented in FIG. 20 by device (0) 622 through device (N-1) 624.

Memory 608 illustratively includes program memory 630, although instructions for execution by CPU 602 could be provided in any of the ways described above. The routines stored in program memory 630 illustratively include scanning routine 640 and readout and combine routine 642. In addition, program memory 630 could store various additional subroutines (not shown) that CPU 602 could call in executing routines 640 and 642.

CPU 602 executes scanning routine 640 to communicate with scanning devices 622 through 624. For example, CPU 602 can receive signals from sensors, perform computations to determine what movements are necessary to obtain a desired scanning motion, and then provide signals to activate motors to produce appropriate relative movement of an optical signal with respect to array 42.

In executing routine 642, CPU 602 can provide signals to each of ICs 612 through 614 to read out subrange cells and to store the photosensed quantities for each spot or other distinguishable part of an optical signal with quantities for each spot or other part of the optical signal combined in an appropriate data structure (not shown), such as by forming a data array or list. Considering the example of FIG. 2, each location $L_m$ would have a distribution of photon energies $D_m$, which could be closely approximated by spectral information from the photosensed quantities in different subranges. A high readout rate with short sensing periods may be necessary to obtain satisfactory resolution. After all of the photosensed quantities for a given location $L_m$ or other part have been read out and combined, CPU 602 can provide them through external I/O 606. Alternatively, all of the photosensed quantities for an entire illuminated field could be combined into a single data structure and provided through external I/O 606 through a suitable streaming operation.

Figure 21:
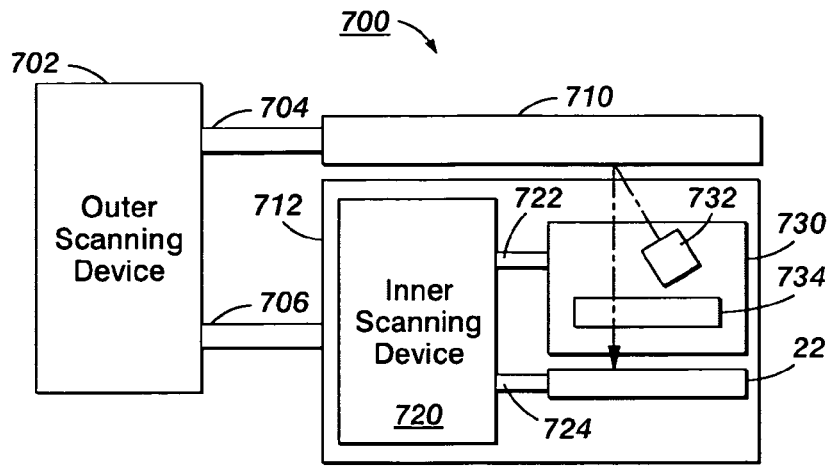
FIG. 21 is a schematic diagram of apparatus with outer and inner scanning devices, in which the outer scanning device can produce relative scanning movement as in FIG. 1.
Figure 22:
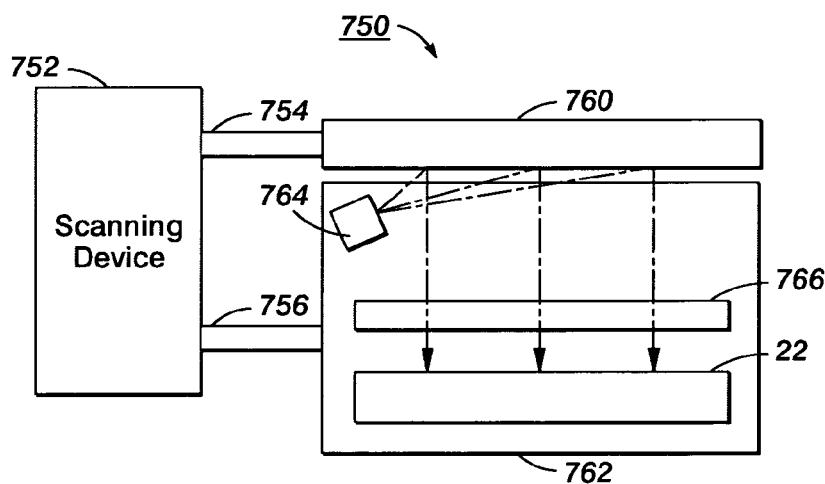
FIG. 22 is a schematic diagram of another apparatus that can produce relative scanning movement as in FIG. 1.
Figure 23:
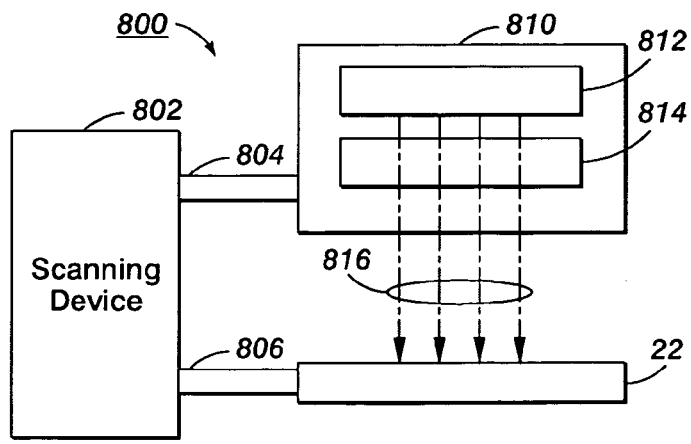
FIG. 23 is a schematic diagram of another apparatus that can produce relative scanning movement as in FIG. 1.

In general, system 600 could be implemented with any scanning devices that produce relative scanning motion, including various conventional scanning and copying devices and foreseeable modifications. Furthermore, system 600 could be implemented for many applications. FIGS. 21-23 illustrate several exemplary types of applications using different scanning techniques, any of which could be implemented with system 600 as in FIG. 20.

FIG. 21 shows apparatus 700, an example of a type of application in which a point-like or line-like optical signal obtained by illuminating an object follows a scan path across array 42 (FIG. 1) in assembly 22. Outer scanning device 702 produces secondary relative scanning movement through motion of one or both of support components 704 and 706. Support component 704 supports object 710, which could, for example, be a sheet of paper, a biochip, or a well plate. Support component 706 supports inner scanning assembly 712, which in turn includes inner scanning device 720.

Inner scanning device 720 produces primary relative scanning movement through motion of one or both of support components 722 and 724. Support component 722 supports optical signal assembly 730, a group of components that must move in a coordinated manner to provide a suitable optical signal. Similarly, support component 724 supports sensing assembly 22, which could be implemented in any of the ways described above.

Within optical signal assembly 730, illumination source 732 illustratively provides point-like or line-like illumination to produce a point-like or line-like optical signal through reflection, as illustrated in FIG. 13. Also, optical component 734 illustratively preserves x-direction resolution of the optical signal during primary relative scanning movement with respect to array 42 (FIG. 1), and can include an array as in FIG. 13.

Apparatus 700 illustrates a type of application in which scanning device 702 provides scanning of all locations of object 710 while scanning device 720 provides scanning of all photon energy subranges for each location of object 710. In controlling apparatus 700, scanning routine 640 in FIG. 20 could provide signals in various ways. For example, device 702 could be controlled to obtain an optical signal from each of a series of locations and, for each location in the series, device 720 could be controlled to produce relative scanning movement of the optical signal across array 42. Or device 720 could be controlled to again produce primary relative scanning movement, providing the optical signal to each of a series of sets of subrange cells in array 42; for each set of cells, device 702 could be controlled to scan all locations of object 710 across each successive set of cells.

FIG. 22 shows apparatus 750, an example of another type of application in which a two-dimensional optical signal obtained by illuminating an object follows a scan path across array 42 (FIG. 1) in assembly 22. The illustrated implementation includes only one scanning device, device 752, which produces relative scanning movement through motion of one or both of support components 754 and 756. Support component 754 supports object 760, which could, for example, be a sheet of paper, a biochip, or a well plate. Support component 756 supports scanning and sensing assembly 762, a group of components that must move in a coordinated manner to provide appropriate relative scanning movement.

Within scanning and sensing assembly 762, illumination source 764 illustratively illuminates a two-dimensional field that includes most or all of the lower surface of object 760, producing a two-dimensional optical signal through reflection. Optical component 766 illustratively preserves both x- and y-direction resolution of the optical signal during relative scanning movement with respect to array 42 in sensing assembly 22, which is also included in assembly 762. As in FIG. 21, sensing assembly 22 could be implemented in any of the ways described above.

In controlling apparatus 750, scanning routine 640 in FIG. 20 could control device 752 to produce relative scanning movement so that the optical signal follows an appropriate scan path across array 42. Readout and combine routine 642 could read out photosensed quantities of photons at a series of positions along the scan path and, based on scanning speed, and could then combine photosensed quantities that indicate spectral information for the same location on object 760 in an appropriate data structure.

FIG. 23 shows apparatus 800, an example of yet another type of application in which a two-dimensional optical signal obtained in any suitable way follows a scan path across array 42 (FIG. 1) in assembly 22. As in FIG. 22, the illustrated implementation includes only one scanning device, device 802, which produces relative scanning movement through motion of one or both of support components 804 and 806. Support component 804 supports optical assembly 810, a group of components that must move in a coordinated manner to provide appropriate relative scanning movement. Similarly, support component 806 supports sensing assembly 22, which could be implemented in any of the ways described above.

Within optical assembly 810, optical signal source 812 can in general be any source of an optical signal that includes spectral information. For example, signal source 812 could include a light source (not shown) that illuminates a surface or one or more stationary or slow-moving objects in any of the ways shown in FIGS. 10-12, or could be an aperture or other appropriate optical component for receiving an external optical signal into optical assembly 810.

Optical component 814 can be implemented like optical component 766 in FIG. 22, preserving both x- and y-direction resolution of the optical signal during relative scanning movement with respect to array 42 in sensing assembly 22. Unlike scanning and sensing component 762 in FIG. 22, however, optical signal assembly 810 does not include sensing assembly 22, and relative scanning movement can therefore occur between assemblies 810 and 22.

In controlling apparatus 800, routines 640 and 642 in FIG. 20 could be performed similarly to the techniques described above in relation to FIG. 22. One possible difference, however, is that optical signal assembly 810 could always be held fixed relative to scanning device 802, such as in a camera application, so that relative scanning movement is accomplished entirely by movement of assembly 22 relative to scanning device 802.

In the implementations of FIGS. 21-23, the various support components are illustratively shown as cantilevered from scanning devices, but support components could generally be implemented with any suitable sizes, shapes, and materials, and could be connected to and controlled by scanning devices in any suitable way. Furthermore, support components could be connected directly or indirectly to the components they support in any appropriate way and could, where appropriate, support an object on a platen or in another suitable way during scanning. In general, relative scanning motion could be accomplished through one or both support components, meaning that, in a specific application, one support component could be stationary.

The implementations of FIGS. 1-23 illustrate examples of apparatus that includes an IC and a scanning device. The IC includes a photosensor array, and the array includes cells that photosense quantities of photons. The scanning device produces relative scanning movement between an optical signal and the array and the optical signal includes photons within an application's range of photon energies. The optical signal follows a scan path across the array along which it is photosensed by cells in the array. In each of two or more segments of the scan path, a respective set of cells in the array photosenses the optical signal. Each segment's set of cells photosenses within a respective subrange, and the subranges of at least two of the segments are different from each other.

The implementations in FIGS. 3-9 further illustrate examples of and methods of producing a transmission structure that transmits photons from the optical signal to each segment's respective set of cells. The transmission structure has a series of regions, each of which transmits photons in a respective segment of the scan path to a respective subset of the cells, and each region transmits within a respective subrange. The respective subranges of at least two of the regions are different.

In specific implementations as in FIG. 20, circuitry responds to quantities photosensed by the respective sets of cells, providing signals indicating spectral information. A system can include the apparatus together with a processor connected to control the scanning device and to read out photosensed quantities from the array. The system can also include a light source that illuminates two-dimensional objects, and the scanning device can respond to the processor by causing relative scanning movement between an illuminated two-dimensional object and the array, while the set of cells also responds by photosensing quantities of photons.

The implementations in FIGS. 1-23 also illustrate examples of a method of sensing optical signals. The method causes relative scanning movement between an optical signal and a photosensor array included in an IC, where the optical signal includes photons within an application's range of photon energies. The optical signal follows a scan path across the array along which cells in the array photosense the optical signal. In each of two or more segments of the scan path, the method uses a respective set of cells in the array to photosense the optical signal. Each segment's set of cells photosenses within a respective subrange, and the subranges of at least two of the segments are different from each other.

In specific implementations, a part of an optical signal follows a line-like path across the array, and the method uses quantities photosensed by the sets of cells as the part of the optical signal follows the line-like path to produce signals indicating spectral information about photons from the part. If the subranges of the segments span substantially the entire range of photon energies, the signals can indicate a complete spectral distribution. Also, if the optical signal is a two-dimensional optical signal, each of its parts can follow a line-like path across the array, such as a row, and the line-like paths can all be parallel.

In specific implementations of FIGS. 1-23, the optical signal emanates from a point-like source and has a line-like scan path; is a line-like optical signal extending in a direction that is approximately perpendicular to the scan path; or is a two-dimensional optical signal with parts that follow line-like paths that are parallel. A line-like optical signal can be obtained by illuminating an object with line-like illumination or by using a line-like aperture. The optical signal can be obtained from a two-dimensional object, such as a sheet-like medium, an array of wells (e.g. a 96-well-plate), or a biochip and from reflected, transmitted, or fluoresced light. A sheet-like medium can, for example, be illuminated to obtain the optical signal from reflected light. An array of wells or biochip can be illuminated from front or back to obtain the optical signal. A biochip with fluidic channels can be illuminated to cause anti-resonant waveguiding, causing an analyte to fluoresce. A lens or lens-like optical component can be used to preserve resolution, such as by imaging the signal. The relative scanning movement can be caused by moving the optical signal, by moving the IC, or both. To obtain the optical signal, relative scanning movement can also be performed between the object and an assembly of components that includes an illumination component.

The implementations in FIGS. 1-23 also illustrate examples of a method in which an optical signal is received at a photosensor array included in an IC. The optical signal includes photons within an application's range of photon energies, and moves along a first direction relative to the array. The method also includes, in each of two or more segments of the first direction, using a respective set of cells to photosense quantities of photons. Each segment's set of cells photosenses within a subrange, and at least two of the segments have different subranges from each other. The method also includes, for each of a set of parts of the signal, combining the photosensed quantities to obtain spectral information for the part.

In general, many additional techniques could be employed in the implementations of FIGS. 1-23, such as adjusting photosensed quantities from subrange cells based on photosensed quantities from reference cells, as described in greater detail in co-pending U.S. patent application Ser. No. 11/316,438, filed Dec. 22, 2005, entitled "Photosensing Throughout Energy Range and in Subranges" and incorporated herein by reference. This adjustment could be performed on analog quantities or, after conversion to digital values, on digital quantities.

Also, similarly to the technique illustrated in FIG. 2, multiple line-like optical signals could be concurrently scanned across array 42 with appropriate sensing periods and techniques for identifying sensed quantities for each optical signal. Suitable operations would be necessary to read out and combine all spectral information for each location in a single scan across a single array. This approach could provide high resolution in both x- and y-directions. It would be possible to use more than one array or to perform more than one scanning operation, while keeping some spacing between consecutive optical signals. Similarly, complete spectral information for an entire two-dimensional illuminated field could be obtained in a single scan across a single array as described above.

Various of the techniques described above have been successfully implemented or simulated, including the production of a detector that includes a commercially available IC covered with a laterally graded Fabry-Perot cavity filter on a glass slide. Wavelength resolution has been experimentally determined and successfully simulated on a computer; based on simulations, it is estimated that techniques as described above will achieve spectral resolution down to $10^{-3}$ nm, spatial resolution down to 10 µm, and spectroscopic scanning of a letter-size in less than 1 min. Anti-resonant waveguide techniques have been successfully tested.

The exemplary implementations described above are advantageous because they can provide compact, inexpensive components to perform functions such as spectrometry of optical signals, and can achieve high spatial and spectral resolution. In general, the techniques can be implemented in existing scanners and printers, including those available in the consumer market. The results of photosensing can be read out rapidly and in parallel from a number of ICs. A number of ICs may be used to address a wide range of photon energies by using suitable coating materials, possibly ranging from the ultraviolet to the far infrared and even into the terahertz range.

Scanning implementations as described above can be applied in various imaging applications, such as document scanners or copiers and digital cameras. Scanning implementations as described above can also be applied in spectrophotometers and other spectroscopic applications for color control or process control or in parallel readout of optical sensors such as two-dimensional photonic crystal sensors or biosensors, whether performing spectroscopy of solids such as semiconductor materials or liquids or aerosols that include bio-particles or other analytes. In addition, relative movement between optical signals and photosensor arrays or other components could be obtained in various ways other than scanning. Also, in the above implementations, photosensor arrays and sources of optical signals are generally illustrated as near each other and as parallel during relative scanning movement, but various other configurations could be used.

The exemplary implementations described above generally rely on transmission structures that include highly reflective interfaces, so that much of the incident light is reflected and only a small fraction reaches the photosensor array. Therefore, the techniques described above are especially useful in applications in which light intensity is very high or a light source emits through a large area or over an extended time. In addition, the above techniques make it possible to increase sensitivity by choosing very long integration times (without loss of throughput capacity), simpler optics, and no dispersion element. By contrast, some conventional systems such as monochromators lose all light defracted into the $0^{th}$, $2^{nd}$, and higher orders. In the implementations described above, very high light yield can be achieved by combining a transmission structure with a highly sensitive photosensor array, such as one that includes avalanche photodetectors.

In addition, components could have various shapes, dimensions, or other numerical or qualitative characteristics other than those illustrated and described above. For example, in the exemplary implementations described above, cells of a photosensor array photosense in different subranges of an application's photon energy range. The subranges of cells could have any appropriate widths and relationships, and could, for example, overlap or be distinct. The width of a cell's subrange can be chosen by designing the transmission structure and the cell sensing area; for example, the width may be as small as 0.1 nm or as great as tens of nanometers.

Some of the above exemplary implementations involve specific materials, such as in photosensor arrays and transmission structures, but the invention could be implemented with a wide variety of materials and with layered structures with various combinations of sublayers. In particular, photosensor arrays for a desired speed, sensitivity and wavelength range could have any suitable material, such as silicon, germanium, indium-gallium-arsenide, gallium arsenide, gallium nitride, or lead sulphide, and could be produced with any appropriate kind of devices, including, for example, photodiodes, avalanche photodiodes, p-i-n diodes, photoconductors, and so forth, with any appropriate technique for sensing and reading out information whether based on CCD, CMOS, or other techniques. Various commercially available detector arrays have pixel densities as high as ten megapixels, and some high density ICs have become relatively inexpensive.

Similarly, transmission structures could be fabricated with any appropriate techniques, including thin film technology such as sputtering, e-beam or thermal evaporation with or without plasma assistance, epitaxial growth, MBE, MOCVD, and so forth. To produce Bragg mirrors, appropriate pairs of materials with low absorption coefficients and large difference in refractive indices could be chosen, bearing in mind the photon energies of interest; exemplary materials include $SiO_2/TiO_2$, $SiO_2/Ta_2O_5$, GaAs/AlAs, and GaAs/AlGaAs. Thicknesses of layer in transmission structures may vary from 30 nm up to a few hundred nanometers. Some of the above exemplary implementations involve particular types of transmission structures, such as Bragg mirrors and paired distributed Bragg reflectors separated by a Fabry-Perot cavity, but these transmission structures are merely exemplary, and any transmission structure that has laterally varying optical thickness could be used. Various techniques could be used to produce transmission structures with lateral variation in addition to those described above, including, during deposition, tilting the substrate, using a shadow mask, or using a temperature gradient to obtain graded layer thickness; also, during homogeneous deposition, off-axis doping, such as by e-beam, MBE, or MOVPE, could produce lateral variation.

Furthermore, various techniques other than transmission structures could be used to obtain photosensor arrays in which cells sense different subranges of photon energy.

Some of the above exemplary implementations employ waveguiding techniques to obtain fluorescence. In general, however, the techniques described above could also be used for self-emitting or auto-fluorescing objects such as particles. Furthermore, various types of fluorescence, photo-luminescence, chemo-fluorescence, inelastic scattering, and so forth could be employed. The technique of anti-resonant waveguiding, described above, is only one of many waveguiding techniques that could be used, and any such waveguiding technique could be applied continuously or intermittently. Various parameters could be adjusted to obtain anti-resonant waveguiding, including the shape of quartz or glass surrounding a layer of fluid or a channel that contains fluid; a thinner structure is generally better, with a surface parallel to the layer or channel generally being required.

Some of the above exemplary implementation use specific illumination techniques or specific optical components to obtain optical signals with desired characteristics, but various other illumination techniques and optical components could be used within the scope of the invention. Furthermore, the above exemplary implementations are described in terms of specific types of two-dimensional objects, but various other objects could be used, and optical signals obtained in various other ways could be photosensed by above-described techniques.

The exemplary implementation in FIG. 20 employs a CPU, which could be a microprocessor or any other appropriate component. Furthermore, as noted above, the adjustment of photosensed quantities could be done either digitally or with analog signals, and could be done either on the same IC as the photosensor array, on other components, or on a combination of the two, with any appropriate combination of software or hardware.

The above exemplary implementations generally involve production and use of photosensor arrays, ICs, transmission structures, illumination techniques, optical components, and scanning devices following particular operations, but different operations could be performed, the order of the operations could be modified, and additional operations could be added within the scope of the invention. For example, in implementations in which a transmission structure is on a separate substrate from a photosensor array, the transmission structure could be moved relative to the photosensor array between consecutive sensing operations. Also, readout of adjusted or unadjusted sensed quantities from an IC could be performed serially or in parallel, and could be performed cell-by-cell or in a streaming operation.

While the invention has been described in conjunction with specific exemplary implementations, it is evident to those skilled in the art that many alternatives, modifications, and variations will be apparent in light of the foregoing description. Accordingly, the invention is intended to embrace all other such alternatives, modifications, and variations that fall within the spirit and scope of the appended claims.

What is claimed is:

1. A method of sensing line-like optical signals, the method comprising:
    obtaining a line-like optical signal;
    causing relative scanning movement between the line-like optical signal and a two-dimensional photosensor array included in an integrated circuit (IC), the optical signal including photons within an application's range of photon energies; the optical signal following a scan path across the array along which cells in the array photosense photons in the optical signal; the scan path extending in a relative movement direction; the line-like optical signal extending in a direction approximately perpendicular to the relative movement direction; and
    in each of two or more segments of the scan path, using a respective line of one or more cells in the array to photosense quantities of photons in the optical signal; each segment's respective line of cells including at least one cell that photosenses photons within a respective subrange of the range of photon energies; the respective subranges of at least two of the segments being different from each other;
    the act of obtaining the line-like optical signal comprising at least one of:
        illuminating a two-dimensional object with line-like illumination to obtain the line-like optical signal;
        using a line-like aperture to obtain the line-like optical signal from a two-dimensional optical signal; and
        using an optical component to prevent the line-like optical signal from spreading in the relative movement direction.

2. The method of claim 1 in which a part of the optical signal follows a line-like path across the array, the method further comprising:
    using quantities photosensed by the respective lines of cells of at least two of the segments as the part of the optical signal follows the line-like path to produce signals indicating spectral information about photons from the part of the optical signal.

3. The method of claim 2 in which the respective subranges of the segments span substantially the entire range of photon energies, the signals indicating a complete spectral distribution of photons from the part of the optical signal.

4. The method of claim 1 in which the act of obtaining the line-like optical signal comprises both of:
    illuminating the two-dimensional object with line-like illumination to obtain the line-like optical signal; and
    using the optical component to prevent the line-like optical signal from spreading in the relative movement direction.

5. The method of claim 1 in which the act of obtaining the line-like optical signal comprises both of:
    using the line-like aperture to obtain the line-like optical signal from the two-dimensional optical signal; and
    using the optical component to prevent the line-like optical signal from spreading in the relative movement direction.

6. The method of claim 1 in which the:
    optical component includes at least one of a lens, a lens array, or a GRIN lens.

7. The method of claim 1 in which the act of obtaining the optical signal further comprises:
    obtaining the optical signal from reflected, transmitted, or fluoresced light.

8. The method of claim 1 in which the act of causing relative scanning movement includes at least one of moving the optical signal and moving the IC.

9. Apparatus comprising: an integrated circuit (IC) that includes a photosensor array; the array including cells that photosense quantities of photons received;
    a scanning device that produces relative scanning movement between an optical signal and the photosensor array, the optical signal including photons within an application's range of photon energies; the optical signal following a scan path across the array along which cells in the array photosense photons in the optical signal; each of a set of one or more parts of the optical signal having a respective distribution of photon energies within the application's range and following a respective line-like path across the array;
    a transmission structure that receives the optical signal along at least part of the scan path and, in response, provides photons to the photosensor array such that, in each of two or more segments of the scan path, a respective set of one or more cells in the array photosenses quantities of photons in the optical signal; each segment's respective set of cells including at least one cell that photosenses photons within a respective subrange of the range of photon energies; the respective subranges of at least two of the segments being different from each other; and
    circuitry that uses quantities photosensed by the respective cells of at least two of the segments as one of the set of parts follows its line-like path to obtain spectral information about the one part's respective distribution of photon energies.

10. The apparatus of claim 9,
    in which the transmission structure has a series of regions, each region transmitting photons from the optical signal in a respective segment of the scan path to a respective subset of the cells, each region transmitting to its respective subset of the cells photons within a respective subrange of the range of photon energies; the respective subranges of at least two of the regions being different.

11. The apparatus of claim 10 in which the transmission structure includes a coating that varies continuously along the scan path, each region in the series of regions including a respective area of the coating.

12. The apparatus of claim 11 in which the coating is over the photosensor array.

13. The apparatus of claim 9
    in which the circuitry further provides signals indicating the spectral information.

14. The apparatus of claim 9 in which the IC includes a CCD or CMOS photosensor array.

15. The apparatus of claim 9 in which the scanning device provides a scanning motion between a two-dimensional object and the photosensor array, the optical signal being obtained by illuminating the two-dimensional object.

16. A system that comprises the apparatus of claim 9, the system further comprising:
    a processor connected to control the scanning device and to read out photosensed quantities of photons from the photosensor array.

17. The system of claim 16 in which the system further comprises a light source that illuminates two-dimensional objects; in response to the processor, the scanning device causing relative scanning movement between an illuminated two-dimensional object and the photosensor array so that an optical signal from the two-dimensional object travels along a scan path across the array; in response to the processor, the sets of cells photosensing quantities of photons in the optical signal.

18. A method comprising:
producing apparatus as in claim 9; the act of producing apparatus including:
producing the apparatus to include:
the IC that includes the photosensor array;
the scanning device that produces relative scanning movement between the optical signal and the photosensor array, the optical signal following the scan path across the array;
the transmission structure; and
the circuitry; and
producing the apparatus so that each of two or more segments of the scan path has a respective set of one or more cells in the array photosensing quantities of photons in the optical signal; each segment's respective set of cells including at least one cell that photosenses photons within a respective subrange of the range of photon energies; the respective subranges of at least two of the segments being different from each other.

19. A method comprising:
receiving an optical signal at a photosensor array included in an integrated circuit (IC), the optical signal including photons within an application's range of photon energies; the received optical signal and the array moving relative to each other along a first direction;
in each of two or more segments of the first direction, using a respective set of one or more cells in the array to photosense quantities of photons in the optical signal; each segment's respective set of cells photosensing photons within a respective subrange of the range of photon energies; the respective subranges of at least two of the segments being different from each other; and
for each of a set of one or more parts of the optical signal, combining quantities photosensed by the respective sets of cells of two or more of the segments to obtain spectral information for the part of the optical signal.

20. The method of claim 19, further comprising:
providing relative scanning movement between the received optical signal and the array.

21. The method of claim 19 in which the respective subranges of the segments span substantially the entire range of photon energies, the act of combining quantities producing a complete spectral distribution for the part of the optical signal.

22. The method of claim 19 in which the optical signal emanates from a point-like source or is a line-like or two-dimensional optical signal.

23. The method of claim 19, further comprising:
obtaining the optical signal from a two-dimensional object.

24. The method of claim 19 in which the optical signal is two-dimensional, the method further comprising: using an optical component to image the two-dimensional optical signal on the array, the optical component including at least one of a lens, a lens array, or a GRIN Lens-like.

25. The method of claim 23 in which the two-dimensional object is a sheet-like medium, an array of wells, or a biochip.

26. The method of claim 23 in which the two-dimensional object is a sheet-like medium and the act of obtaining the optical signal comprises:
illuminating the sheet-like medium to obtain the optical signal from reflected light.

27. The method of claim 23 in which the two-dimensional object is an array of wells disposed toward a forward side and the act of obtaining the optical signal comprises:
illuminating the array of wells from the forward side or from a back side opposite the forward side to obtain the optical signal.

28. The method of claim 23 in which the two-dimensional object is a fluidic structure with a channel containing an analyte and the act of obtaining the optical signal comprises:
providing excitation to the fluidic structure to cause the analyte to fluoresce.

29. The method of claim 28 in which the two-dimensional object is a biochip and the channel contains fluid; the act of providing excitation illuminating the channel to cause anti-resonant waveguiding.

30. The method of claim 23 in which the act of obtaining the optical signal comprising:
causing relative scanning movement between the two-dimensional object and an assembly of components, the assembly of components including an illumination source.

31. The method of claim 19 in which the respective sets of cells of the segments are distinct, with no shared cells.

32. Apparatus comprising:
an assembly including:
a two-dimensional photosensor array; and
a transmission structure;
a scanning device that produces relative scanning movement in a relative movement direction between an optical signal and the assembly, the optical signal including photons within an application's range of photon energies; the optical signal following a scan path across the array along which cells in the array photosense photons in the optical signal; the transmission structure receiving the optical signal along at least part of the scan path and, in response, providing photons to the photosensor array such that, in each of two or more segments of the scan path, a respective set of one or more cells in the array photosenses quantities of photons from the transmission structure; each segment's respective set of cells extending in an orthogonal direction perpendicular to the relative movement direction and including at least one cell that photosenses photons within a respective subrange of the range of photon energies; the respective subranges of at least two of the segments being different from each other; and
an optical component that receives the optical signal and provides it to the transmission structure; the optical component performing at least one of:
preserving resolution of the optical signal in the relative movement direction;
preserving resolution of the optical signal in the orthogonal direction; and
imaging the optical signal onto the photosensor array.

33. The apparatus of claim 32 in which the optical component includes at least one of:
a lens;
a lens array; and
GRIN lens.

* * * * *